United States Patent
Rios et al.

(10) Patent No.: US 11,730,543 B2
(45) Date of Patent: Aug. 22, 2023

(54) SENSORY ENHANCED ENVIRONMENTS FOR INJECTION AID AND SOCIAL TRAINING

(71) Applicant: Truinject Corp., Irvine, CA (US)

(72) Inventors: Gabrielle A. Rios, Newport Beach, CA (US); Clark B. Foster, Newport Beach, CA (US)

(73) Assignee: Truinject Corp., Irvine, CA (US)

( * ) Notice: Subject to any disclaimer, the term of this patent is extended or adjusted under 35 U.S.C. 154(b) by 215 days.

(21) Appl. No.: 17/084,379

(22) Filed: Oct. 29, 2020

(65) Prior Publication Data
US 2021/0177518 A1    Jun. 17, 2021

Related U.S. Application Data

(63) Continuation of application No. 15/448,364, filed on Mar. 2, 2017, now Pat. No. 10,849,688.
(Continued)

(51) Int. Cl.
*A61B 34/10*     (2016.01)
*G16H 40/63*   (2018.01)
(Continued)

(52) U.S. Cl.
CPC .............. *A61B 34/10* (2016.02); *A61B 34/20* (2016.02); *A61B 34/25* (2016.02); *A61B 90/36* (2016.02);
(Continued)

(58) Field of Classification Search
CPC ......... A61B 34/10; A61B 34/20; A61B 34/25; A61B 90/36; G16H 50/50; G16H 40/63; G06F 19/00; G09B 23/285
See application file for complete search history.

(56) References Cited

U.S. PATENT DOCUMENTS

| | | |
|---|---|---|
| 3,237,340 A | 3/1966 | Knott |
| 3,722,108 A | 3/1973 | Chase |

(Continued)

FOREIGN PATENT DOCUMENTS

| | | |
|---|---|---|
| AU | 2011218649 B2 | 9/2011 |
| AU | 2015255197 A1 | 12/2015 |

(Continued)

OTHER PUBLICATIONS

3D Systems, "Angio Mentor Clinical Validations, The Role of Simulation in Boosting the learning Curve in EVAR Procedures," Journal of Surgical Education, Mar.-Apr. 2018, 75(2), pp. 1-2, accessed on Feb. 6, 2020, https://simbionix.com/ simulators/clinical-validations/angio-mentor-clinical-validations/ (listing clinical validations completed on ANGIO Mentor from 2007 through 2018).

(Continued)

Primary Examiner — Robert P Bullington
(74) Attorney, Agent, or Firm — Knobbe, Martens, Olson & Bear, LLP

(57) ABSTRACT

An injection aid system and a social aid system having a computing system with at least one processor and a memory device. The computing system can be configured to generate a at least one of a virtual environment and an augmented environment. A display device can be coupled to the computing system and configured to visually display the environment. The injection aid system can further include an injection tool and a treatment target configured to receive a simulated injection by the injection tool. The injection tool can have a needle and a plunger.

19 Claims, 17 Drawing Sheets

Related U.S. Application Data

(60) Provisional application No. 62/302,646, filed on Mar. 2, 2016, provisional application No. 62/399,252, filed on Sep. 23, 2016.

(51) Int. Cl.
  *G16H 50/50* (2018.01)
  *A61B 34/20* (2016.01)
  *A61B 34/00* (2016.01)
  *A61B 90/00* (2016.01)
  *G09B 23/28* (2006.01)
  *A61B 17/34* (2006.01)
  *A61B 90/50* (2016.01)

(52) U.S. Cl.
  CPC .......... *G09B 23/285* (2013.01); *G16H 40/63* (2018.01); *G16H 50/50* (2018.01); *A61B 17/3403* (2013.01); *A61B 2034/104* (2016.02); *A61B 2034/105* (2016.02); *A61B 2034/107* (2016.02); *A61B 2034/2055* (2016.02); *A61B 2034/2072* (2016.02); *A61B 2090/365* (2016.02); *A61B 2090/502* (2016.02)

(56) References Cited

U.S. PATENT DOCUMENTS

| | | |
|---|---|---|
| 3,941,121 A | 3/1976 | Olinger et al. |
| 4,142,517 A | 3/1979 | Contreras Guerrero de Stavropoulos et al. |
| 4,311,138 A | 1/1982 | Sugarman |
| 4,356,828 A | 11/1982 | Jamshidi |
| 4,410,020 A | 10/1983 | Lorenz |
| 4,439,162 A | 3/1984 | Blaine |
| 4,515,168 A | 5/1985 | Chester et al. |
| 4,566,438 A | 1/1986 | Liese et al. |
| 4,836,632 A | 6/1989 | Bardoorian |
| 4,867,686 A | 9/1989 | Goldstein |
| 4,880,971 A | 11/1989 | Danisch |
| 4,945,478 A | 7/1990 | Merickel et al. |
| 5,065,236 A | 11/1991 | Diner |
| 5,197,476 A | 3/1993 | Nowacki et al. |
| 5,198,877 A | 3/1993 | Schulz |
| 5,241,184 A | 8/1993 | Menzel |
| 5,249,581 A | 10/1993 | Horbal et al. |
| 5,295,483 A | 3/1994 | Nowacki et al. |
| 5,321,257 A | 6/1994 | Danisch |
| 5,391,081 A | 2/1995 | Lampotang et al. |
| 5,517,997 A | 5/1996 | Fontenot |
| 5,518,407 A | 5/1996 | Greenfield et al. |
| 5,534,704 A | 7/1996 | Robinson et al. |
| 5,622,170 A | 4/1997 | Shulz |
| 5,651,783 A | 7/1997 | Reynard |
| 5,690,618 A | 11/1997 | Smith et al. |
| 5,704,791 A | 1/1998 | Gillio |
| 5,727,948 A | 3/1998 | Jordan |
| 5,766,016 A | 8/1998 | Sinclair et al. |
| 5,817,105 A | 10/1998 | Van Der Brug |
| 5,828,770 A | 10/1998 | Leis et al. |
| 5,890,908 A | 4/1999 | Lampotang et al. |
| 5,899,692 A | 5/1999 | Davis et al. |
| 5,923,417 A | 7/1999 | Leis |
| 5,954,648 A | 9/1999 | Van Der Brug |
| 5,954,701 A | 9/1999 | Matalon |
| 6,010,531 A | 1/2000 | Donlon et al. |
| 6,024,576 A | 2/2000 | Bevirt et al. |
| 6,061,644 A | 5/2000 | Leis |
| 6,064,749 A | 5/2000 | Hirota et al. |
| 6,127,672 A | 10/2000 | Danisch |
| 6,172,499 B1 | 1/2001 | Ashe |
| 6,217,558 B1 | 4/2001 | Zadini et al. |
| 6,288,785 B1 | 9/2001 | Frantz et al. |
| 6,353,226 B1 | 3/2002 | Khalil et al. |
| 6,385,482 B1 | 5/2002 | Boksberger et al. |
| 6,428,323 B1 | 8/2002 | Pugh |
| 6,470,302 B1 | 10/2002 | Cunningham et al. |
| 6,485,308 B1 | 11/2002 | Goldstein |
| 6,538,634 B1 | 3/2003 | Chui et al. |
| 6,553,326 B1 | 4/2003 | Kirsch et al. |
| 6,564,087 B1 | 5/2003 | Pitris et al. |
| 6,568,941 B1 | 5/2003 | Goldstein |
| 6,575,757 B1 | 6/2003 | Leight et al. |
| 6,625,563 B2 | 9/2003 | Kirsch et al. |
| 6,687,529 B2 | 2/2004 | Van Vaals |
| 6,702,790 B1 | 3/2004 | Ross et al. |
| 6,769,286 B2 | 8/2004 | Biermann et al. |
| 6,774,624 B2 | 8/2004 | Anderson et al. |
| 6,836,745 B2 | 12/2004 | Seiler et al. |
| 6,857,878 B1 | 2/2005 | Chosack et al. |
| 6,863,536 B1 | 3/2005 | Fisher et al. |
| 7,015,859 B2 | 3/2006 | Anderson |
| 7,115,113 B2 | 10/2006 | Evans et al. |
| 7,137,712 B2 | 11/2006 | Brunner et al. |
| 7,158,754 B2 | 1/2007 | Anderson |
| 7,194,296 B2 | 3/2007 | Frantz et al. |
| 7,204,796 B1 | 4/2007 | Seiler |
| 7,247,149 B2 | 7/2007 | Beyerlein |
| 7,383,728 B2 | 6/2008 | Noble et al. |
| 7,474,776 B2 | 1/2009 | Kaufman et al. |
| 7,500,853 B2 | 3/2009 | Bevirt et al. |
| 7,544,062 B1 | 6/2009 | Hauschild et al. |
| 7,553,159 B1 | 6/2009 | Arnal et al. |
| 7,594,815 B2 | 9/2009 | Toly |
| 7,665,995 B2 | 2/2010 | Toly |
| 7,725,279 B2 | 5/2010 | Luinge et al. |
| 7,761,139 B2 | 7/2010 | Tearney et al. |
| 7,783,441 B2 | 8/2010 | Nieminen et al. |
| 7,857,626 B2 | 12/2010 | Toly |
| 7,912,662 B2 | 3/2011 | Zuhars et al. |
| 7,945,311 B2 | 5/2011 | McCloy et al. |
| 8,007,281 B2 | 8/2011 | Toly |
| 8,040,127 B2 | 10/2011 | Jensen |
| 8,072,606 B2 | 12/2011 | Chau et al. |
| 8,103,883 B2 | 1/2012 | Smith |
| 8,131,342 B2 | 3/2012 | Anderson |
| 8,165,844 B2 | 4/2012 | Luinge et al. |
| 8,203,487 B2 | 6/2012 | Hol et al. |
| 8,208,716 B2 | 6/2012 | Choi et al. |
| 8,226,610 B2 | 7/2012 | Edwards et al. |
| 8,250,921 B2 | 8/2012 | Nasiri et al. |
| 8,257,250 B2 | 9/2012 | Tenger et al. |
| 8,277,411 B2 | 10/2012 | Gellman |
| 8,319,182 B1 | 11/2012 | Brady et al. |
| 8,342,853 B2 | 1/2013 | Cohen |
| 8,351,773 B2 | 1/2013 | Nasiri et al. |
| 8,382,485 B2 | 2/2013 | Bardsley et al. |
| 8,403,888 B2 | 3/2013 | Gaudet |
| 8,408,918 B2 | 4/2013 | Hu et al. |
| 8,409,140 B2 | 4/2013 | Ejlersen et al. |
| 8,437,833 B2 | 5/2013 | Silverstein |
| 8,442,619 B2 | 5/2013 | Li et al. |
| 8,450,997 B2 | 5/2013 | Silverman |
| 8,467,855 B2 | 6/2013 | Yasui |
| 8,469,716 B2 | 6/2013 | Fedotov et al. |
| 8,525,990 B2 | 9/2013 | Wilcken |
| 8,535,062 B2 | 9/2013 | Nguyen |
| 8,556,635 B2 | 10/2013 | Toly |
| 8,632,498 B2 | 1/2014 | Rimsa et al. |
| 8,647,124 B2 | 2/2014 | Bardsley et al. |
| 8,655,622 B2 | 2/2014 | Yen et al. |
| 8,684,744 B2 | 4/2014 | Selz et al. |
| 8,689,801 B2 | 4/2014 | Ritchey et al. |
| 8,715,233 B2 | 5/2014 | Brewer et al. |
| 8,764,449 B2 | 7/2014 | Rios et al. |
| 8,818,751 B2 | 8/2014 | Van Acht et al. |
| 8,917,916 B2 | 12/2014 | Martin et al. |
| 8,924,334 B2 | 12/2014 | Lacey et al. |
| 8,945,147 B2 | 2/2015 | Ritchey et al. |
| 8,961,189 B2 | 2/2015 | Rios et al. |
| 8,994,366 B2 | 3/2015 | Ashe |
| 9,017,080 B1 | 4/2015 | Placik |
| 9,024,624 B2 | 5/2015 | Brunner |
| 9,031,314 B2 | 5/2015 | Clausen et al. |
| 9,053,641 B2 | 6/2015 | Samosky |

(56) References Cited

U.S. PATENT DOCUMENTS

| | | |
|---|---|---|
| 9,123,261 B2 | 9/2015 | Lowe |
| 9,251,721 B2 | 2/2016 | Lampotang et al. |
| 9,275,557 B2 | 3/2016 | Trotta |
| 9,318,032 B2 | 4/2016 | Samosky et al. |
| 9,361,809 B1 | 6/2016 | Caron |
| 9,439,653 B2 | 9/2016 | Avneri et al. |
| 9,443,446 B2 | 9/2016 | Rios et al. |
| 9,456,766 B2 | 10/2016 | Cox et al. |
| 9,460,638 B2 | 10/2016 | Baker et al. |
| 9,486,162 B2 | 11/2016 | Zhuang et al. |
| 9,554,716 B2 | 1/2017 | Burnside et al. |
| 9,595,208 B2 | 3/2017 | Ottensmeyer et al. |
| 9,626,805 B2 | 4/2017 | Lampotang et al. |
| 9,666,102 B2 | 5/2017 | East et al. |
| 9,792,836 B2 | 10/2017 | Rios et al. |
| 9,922,578 B2 | 3/2018 | Foster et al. |
| 10,083,630 B2 | 9/2018 | Samosky et al. |
| 10,173,015 B2 | 1/2019 | Fiedler et al. |
| 10,269,266 B2 | 4/2019 | Rios et al. |
| 10,290,231 B2 | 5/2019 | Rios et al. |
| 10,290,232 B2 | 5/2019 | Rios et al. |
| 10,325,522 B2 | 6/2019 | Samosky et al. |
| 10,398,855 B2 * | 9/2019 | McClellan ............ A61M 5/427 |
| 10,500,340 B2 | 12/2019 | Rios et al. |
| 10,643,497 B2 | 5/2020 | Rios et al. |
| 10,743,942 B2 | 8/2020 | Foster et al. |
| 10,849,688 B2 | 12/2020 | Rios et al. |
| 10,857,306 B2 | 12/2020 | Holmqvist et al. |
| 10,896,627 B2 | 1/2021 | Foster et al. |
| 10,902,746 B2 | 1/2021 | Rios et al. |
| 11,403,964 B2 | 8/2022 | Rios et al. |
| 2001/0037191 A1 | 11/2001 | Furuta et al. |
| 2002/0076681 A1 | 6/2002 | Leight et al. |
| 2002/0168618 A1 | 11/2002 | Anderson et al. |
| 2002/0191000 A1 | 12/2002 | Henn |
| 2003/0031993 A1 | 2/2003 | Pugh |
| 2003/0055380 A1 | 3/2003 | Flaherty |
| 2003/0065278 A1 | 4/2003 | Rubinstenn et al. |
| 2003/0108853 A1 | 6/2003 | Chosack et al. |
| 2003/0114842 A1 | 6/2003 | DiStefano |
| 2003/0164401 A1 | 9/2003 | Andreasson et al. |
| 2003/0220557 A1 | 11/2003 | Cleary et al. |
| 2004/0009459 A1 | 1/2004 | Anderson et al. |
| 2004/0092878 A1 | 5/2004 | Flaherty |
| 2004/0118225 A1 | 6/2004 | Wright et al. |
| 2004/0126746 A1 | 7/2004 | Toly |
| 2004/0175684 A1 | 9/2004 | Kaasa et al. |
| 2004/0234933 A1 | 11/2004 | Dawson et al. |
| 2005/0055241 A1 | 3/2005 | Horstmann |
| 2005/0057243 A1 | 3/2005 | Johnson et al. |
| 2005/0070788 A1 | 3/2005 | Wilson et al. |
| 2005/0084833 A1 | 4/2005 | Lacey et al. |
| 2005/0181342 A1 | 8/2005 | Toly |
| 2005/0203380 A1 | 9/2005 | Sauer et al. |
| 2006/0084050 A1 | 4/2006 | Haluck |
| 2006/0085068 A1 | 4/2006 | Barry |
| 2006/0194180 A1 | 8/2006 | Bevirt et al. |
| 2006/0264745 A1 | 11/2006 | Da Silva |
| 2006/0264967 A1 | 11/2006 | Ferreyro et al. |
| 2007/0003917 A1 | 1/2007 | Kitching et al. |
| 2007/0150247 A1 | 6/2007 | Bodduluri |
| 2007/0179448 A1 | 8/2007 | Lim et al. |
| 2007/0197954 A1 | 8/2007 | Keenan |
| 2007/0219503 A1 | 9/2007 | Loop et al. |
| 2007/0238981 A1 | 10/2007 | Zhu et al. |
| 2008/0038703 A1 | 2/2008 | Segal et al. |
| 2008/0097378 A1 | 4/2008 | Zuckerman |
| 2008/0107305 A1 | 5/2008 | Vanderkooy et al. |
| 2008/0123910 A1 | 5/2008 | Zhu |
| 2008/0138781 A1 | 6/2008 | Pellegrin et al. |
| 2008/0176198 A1 | 7/2008 | Ansari et al. |
| 2008/0177174 A1 | 7/2008 | Crane |
| 2008/0194973 A1 | 8/2008 | Imam |
| 2008/0270175 A1 | 10/2008 | Rodriguez et al. |
| 2009/0036902 A1 | 2/2009 | Dimaio et al. |
| 2009/0043253 A1 | 2/2009 | Podaima |
| 2009/0046140 A1 | 2/2009 | Lashmet et al. |
| 2009/0061404 A1 | 3/2009 | Toly |
| 2009/0074262 A1 | 3/2009 | Kudavelly |
| 2009/0081619 A1 | 3/2009 | Miasnik |
| 2009/0081627 A1 | 3/2009 | Ambrozio |
| 2009/0123896 A1 | 5/2009 | Hu et al. |
| 2009/0142741 A1 | 6/2009 | Ault et al. |
| 2009/0161827 A1 | 6/2009 | Gertner et al. |
| 2009/0208915 A1 | 8/2009 | Pugh |
| 2009/0221908 A1 | 9/2009 | Glossop |
| 2009/0263775 A1 | 10/2009 | Ullrich |
| 2009/0265671 A1 | 10/2009 | Sachs et al. |
| 2009/0275810 A1 | 11/2009 | Ayers et al. |
| 2009/0278791 A1 | 11/2009 | Slycke et al. |
| 2009/0305213 A1 | 12/2009 | Burgkart et al. |
| 2009/0326556 A1 | 12/2009 | Diolaiti |
| 2010/0030111 A1 | 2/2010 | Perriere |
| 2010/0071467 A1 | 3/2010 | Nasiri et al. |
| 2010/0099066 A1 | 4/2010 | Mire et al. |
| 2010/0120006 A1 | 5/2010 | Bell |
| 2010/0167249 A1 | 7/2010 | Ryan |
| 2010/0167250 A1 | 7/2010 | Ryan et al. |
| 2010/0167254 A1 | 7/2010 | Nguyen |
| 2010/0179428 A1 | 7/2010 | Pederson et al. |
| 2010/0198141 A1 | 8/2010 | Laitenberger et al. |
| 2010/0273135 A1 | 10/2010 | Cohen |
| 2011/0027767 A1 | 2/2011 | Divinagracia |
| 2011/0046915 A1 | 2/2011 | Hol et al. |
| 2011/0060229 A1 | 3/2011 | Hulvershorn et al. |
| 2011/0071419 A1 | 3/2011 | Liu et al. |
| 2011/0098569 A1 | 4/2011 | Warmath et al. |
| 2011/0144658 A1 | 6/2011 | Wenderow et al. |
| 2011/0170752 A1 | 7/2011 | Martin et al. |
| 2011/0202012 A1 | 8/2011 | Bartlett |
| 2011/0207102 A1 | 8/2011 | Trotta et al. |
| 2011/0236866 A1 | 9/2011 | Psaltis et al. |
| 2011/0257596 A1 | 10/2011 | Gaudet |
| 2011/0269109 A2 | 11/2011 | Miyazaki |
| 2011/0282188 A1 | 11/2011 | Burnside et al. |
| 2011/0294103 A1 | 12/2011 | Segal et al. |
| 2011/0301500 A1 | 12/2011 | Maguire et al. |
| 2011/0306025 A1 | 12/2011 | Sheehan et al. |
| 2012/0002014 A1 | 1/2012 | Walsh |
| 2012/0015336 A1 | 1/2012 | Mach |
| 2012/0026307 A1 | 2/2012 | Price |
| 2012/0027269 A1 | 2/2012 | Fidaleo et al. |
| 2012/0034587 A1 | 2/2012 | Toly |
| 2012/0045743 A1 | 2/2012 | Okano et al. |
| 2012/0053514 A1 | 3/2012 | Robinson et al. |
| 2012/0082969 A1 | 4/2012 | Schwartz et al. |
| 2012/0130269 A1 | 5/2012 | Rea |
| 2012/0148994 A1 | 6/2012 | Hori et al. |
| 2012/0157800 A1 | 6/2012 | Tschen |
| 2012/0171652 A1 | 7/2012 | Sparks et al. |
| 2012/0183238 A1 | 7/2012 | Savvides et al. |
| 2012/0209243 A1 | 8/2012 | Yan |
| 2012/0214144 A1 | 8/2012 | Trotta et al. |
| 2012/0219937 A1 | 8/2012 | Hughes |
| 2012/0238875 A1 | 9/2012 | Savitsky et al. |
| 2012/0251987 A1 | 10/2012 | Huang et al. |
| 2012/0280988 A1 | 11/2012 | Lampotang et al. |
| 2012/0282583 A1 | 11/2012 | Thaler et al. |
| 2012/0293632 A1 | 11/2012 | Yukich |
| 2012/0301858 A1 | 11/2012 | Park et al. |
| 2012/0323520 A1 | 12/2012 | Keal |
| 2013/0006178 A1 | 1/2013 | Pinho et al. |
| 2013/0018494 A1 | 1/2013 | Amini |
| 2013/0046489 A1 | 2/2013 | Keal |
| 2013/0100256 A1 | 4/2013 | Kirk et al. |
| 2013/0131503 A1 | 5/2013 | Schneider et al. |
| 2013/0179110 A1 | 7/2013 | Lee |
| 2013/0189658 A1 | 7/2013 | Peters et al. |
| 2013/0189663 A1 | 7/2013 | Tuchschmid et al. |
| 2013/0197845 A1 | 8/2013 | Keal |
| 2013/0198625 A1 | 8/2013 | Anderson |
| 2013/0203032 A1 | 8/2013 | Bardsley |
| 2013/0223673 A1 | 8/2013 | Davis et al. |
| 2013/0236872 A1 | 9/2013 | Laurusonis et al. |

(56) References Cited

U.S. PATENT DOCUMENTS

| | | |
|---|---|---|
| 2013/0267838 A1 | 10/2013 | Frank et al. |
| 2013/0296691 A1 | 11/2013 | Ashe |
| 2013/0308827 A1 | 11/2013 | Dillavou et al. |
| 2013/0323700 A1 | 12/2013 | Samosky et al. |
| 2013/0342657 A1 | 12/2013 | Robertson |
| 2014/0017650 A1 | 1/2014 | Romero |
| 2014/0039452 A1 | 2/2014 | Bangera et al. |
| 2014/0071165 A1 | 3/2014 | Tuchschmid et al. |
| 2014/0102167 A1 | 4/2014 | MacNeil et al. |
| 2014/0121636 A1 | 5/2014 | Boyden et al. |
| 2014/0121637 A1* | 5/2014 | Boyden ............... A61M 5/427 604/116 |
| 2014/0129200 A1 | 5/2014 | Bronstein et al. |
| 2014/0142422 A1 | 5/2014 | Manzke et al. |
| 2014/0162232 A1 | 6/2014 | Yang et al. |
| 2014/0240314 A1 | 8/2014 | Fukazawa et al. |
| 2014/0244209 A1 | 8/2014 | Lee et al. |
| 2014/0260704 A1 | 9/2014 | Lloyd et al. |
| 2014/0278183 A1 | 9/2014 | Zheng et al. |
| 2014/0278205 A1 | 9/2014 | Bhat et al. |
| 2014/0278215 A1 | 9/2014 | Keal et al. |
| 2014/0322683 A1 | 10/2014 | Baym et al. |
| 2014/0349263 A1 | 11/2014 | Shabat et al. |
| 2014/0349266 A1 | 11/2014 | Choi |
| 2014/0363801 A1 | 12/2014 | Samosky et al. |
| 2015/0031987 A1 | 1/2015 | Pameijer et al. |
| 2015/0049081 A1 | 2/2015 | Coffey et al. |
| 2015/0079545 A1 | 3/2015 | Kurtz |
| 2015/0079565 A1 | 3/2015 | Miller et al. |
| 2015/0080710 A1 | 3/2015 | Henkel et al. |
| 2015/0086955 A1 | 3/2015 | Poniatowski et al. |
| 2015/0182706 A1 | 7/2015 | Wurmbauer et al. |
| 2015/0206456 A1 | 7/2015 | Foster et al. |
| 2015/0262512 A1 | 9/2015 | Rios et al. |
| 2015/0314105 A1 | 11/2015 | Gasparyan et al. |
| 2015/0352294 A1 | 12/2015 | O'Mahoney et al. |
| 2015/0359721 A1 | 12/2015 | Hagel et al. |
| 2015/0379899 A1 | 12/2015 | Baker et al. |
| 2015/0379900 A1 | 12/2015 | Samosky et al. |
| 2016/0000411 A1 | 1/2016 | Raju et al. |
| 2016/0001016 A1 | 1/2016 | Poulsen et al. |
| 2016/0155363 A1 | 6/2016 | Rios et al. |
| 2016/0193428 A1 | 7/2016 | Perthu |
| 2016/0213856 A1 | 7/2016 | Despa et al. |
| 2016/0293058 A1 | 10/2016 | Galliot et al. |
| 2016/0324580 A1* | 11/2016 | Esterberg ............... A61B 34/10 |
| 2016/0374902 A1 | 12/2016 | Govindasamy et al. |
| 2017/0053563 A1 | 2/2017 | Holloway |
| 2017/0178540 A1 | 6/2017 | Rios et al. |
| 2017/0186339 A1 | 6/2017 | Rios et al. |
| 2017/0245943 A1 | 8/2017 | Foster et al. |
| 2017/0252108 A1 | 9/2017 | Rios et al. |
| 2017/0254636 A1 | 9/2017 | Foster et al. |
| 2017/0316720 A1 | 11/2017 | Singh et al. |
| 2018/0012516 A1 | 1/2018 | Rios et al. |
| 2018/0068075 A1 | 3/2018 | Shiwaku |
| 2018/0197441 A1 | 7/2018 | Rios et al. |
| 2018/0225991 A1 | 8/2018 | Pedroso et al. |
| 2018/0261125 A1 | 9/2018 | Rios et al. |
| 2018/0261126 A1 | 9/2018 | Rios et al. |
| 2018/0271581 A1 | 9/2018 | OuYang et al. |
| 2018/0333543 A1 | 11/2018 | Diaz et al. |
| 2018/0338806 A1 | 11/2018 | Grubbs |
| 2019/0130792 A1 | 5/2019 | Rios et al. |
| 2020/0202747 A1 | 6/2020 | Rios et al. |
| 2020/0206424 A1 | 7/2020 | Rios et al. |
| 2020/0226951 A1 | 7/2020 | Rios et al. |
| 2021/0174706 A1 | 6/2021 | Rios et al. |
| 2021/0213205 A1 | 7/2021 | Karlsson et al. |
| 2022/0309954 A1 | 9/2022 | Rios et al. |
| 2023/0009855 A1 | 1/2023 | Rios et al. |

FOREIGN PATENT DOCUMENTS

| | | |
|---|---|---|
| CA | 2865236 A1 | 9/2013 |
| CN | 2751386 Y | 1/2006 |
| CN | 201213049 Y | 3/2009 |
| CN | 201359805 Y | 12/2009 |
| CN | 201465399 U | 5/2010 |
| CN | 101908294 A | 12/2010 |
| CN | 202159452 U | 3/2012 |
| CN | 102708745 A | 10/2012 |
| CN | 102737533 A | 10/2012 |
| CN | 104703641 A | 6/2015 |
| CN | 105118350 A | 12/2015 |
| CN | 205541594 U | 8/2016 |
| CN | 106710413 A | 5/2017 |
| CN | 107067856 A | 8/2017 |
| DE | 102004046003 A1 | 3/2006 |
| DE | 202005021286 U1 | 9/2007 |
| EP | 0316763 A1 | 5/1989 |
| EP | 1504713 A1 | 2/2005 |
| EP | 1723977 A1 | 11/2006 |
| EP | 1884211 A2 | 2/2008 |
| EP | 2425416 B1 | 3/2015 |
| EP | 2538398 B1 | 8/2015 |
| EP | 2756857 B1 | 5/2016 |
| GB | 2288686 B | 7/1997 |
| GB | 2309644 A | 8/1997 |
| GB | 2 309 644 B | 5/2000 |
| GB | 2508510 | 6/2014 |
| IN | 201202900 P1 | 11/2013 |
| JP | H10161522 A | 6/1998 |
| JP | H10260627 A | 9/1998 |
| JP | 2004-348095 A | 12/2004 |
| JP | 2006-189525 A | 7/2006 |
| JP | 2008-83624 A | 4/2008 |
| JP | 2011-113056 A | 6/2011 |
| JP | 2013-037088 A | 2/2013 |
| JP | 52-21420 | 6/2013 |
| JP | 2013-250453 A | 12/2013 |
| JP | 2014-153482 A | 8/2014 |
| KR | 2012009379 A | 2/2012 |
| KR | 20140047943 A | 4/2014 |
| KR | 10-1397522 B1 | 5/2014 |
| TW | 201207785 A | 2/2012 |
| WO | WO 96/16389 | 5/1996 |
| WO | WO 00/53115 | 9/2000 |
| WO | WO 02/083003 | 10/2002 |
| WO | WO 2005/083653 | 9/2005 |
| WO | WO 2005/089835 | 9/2005 |
| WO | WO 2007/109540 | 9/2007 |
| WO | WO 2008/005315 A2 | 1/2008 |
| WO | WO 2008/122006 A1 | 10/2008 |
| WO | WO 2009/023247 A1 | 2/2009 |
| WO | WO 2009/049082 | 4/2009 |
| WO | WO 2009/094646 | 7/2009 |
| WO | WO 2009/141769 | 11/2009 |
| WO | WO 2011/043645 | 4/2011 |
| WO | WO 2011/127379 | 10/2011 |
| WO | WO 2011/136778 | 11/2011 |
| WO | WO 2012/075166 | 6/2012 |
| WO | WO 2012/088471 A1 | 6/2012 |
| WO | WO 2012/101286 | 8/2012 |
| WO | WO 2012/106706 | 8/2012 |
| WO | WO 2012/155056 | 11/2012 |
| WO | WO 2013/025639 | 2/2013 |
| WO | WO 2013/064804 | 5/2013 |
| WO | WO 2014/035659 | 3/2014 |
| WO | WO 2014/070799 | 5/2014 |
| WO | WO 2014/100658 | 6/2014 |
| WO | WO 2015/109251 | 7/2015 |
| WO | WO 2015/110327 A1 | 7/2015 |
| WO | WO 2015/136564 | 9/2015 |
| WO | WO 2015/138608 | 9/2015 |
| WO | WO 2015/171778 | 11/2015 |
| WO | WO 2016/089706 | 6/2016 |
| WO | WO 2016/123144 A2 | 8/2016 |
| WO | WO 2016/162298 | 10/2016 |
| WO | WO 2016/191127 | 12/2016 |
| WO | WO 2017/048929 A1 | 3/2017 |

(56) References Cited

FOREIGN PATENT DOCUMENTS

| WO | WO 2017/048931 A1 | 3/2017 |
|---|---|---|
| WO | WO 2017/050781 A1 | 3/2017 |
| WO | WO 2017/060017 A1 | 4/2017 |
| WO | WO 2017/070391 | 4/2017 |
| WO | WO 2017/151441 | 9/2017 |
| WO | WO 2017/151716 | 9/2017 |
| WO | WO 2017/151963 | 9/2017 |
| WO | WO 2017/153077 | 9/2017 |
| WO | WO 2018/136901 | 7/2018 |

OTHER PUBLICATIONS

3D Systems, "Angio Mentor™," Product Brochure/Overview. 2015, 6 pp.
Dimension Engineering, Internet Archive Wayback Machine webpage capture of https://www.dimensionengineering.com/info/accelerometers, apparently available Apr. 11, 2012, site visited Aug. 24, 2020.
"Accelerometer: Introduction to Acceleration Measurement," Omega Engineering, Sep. 17, 2015, 3 pages, https://www.omega.com/prodinfo/accelerometers.html.
Afzal, et al., "Use of Earth's Magnetic Field for Mitigating Gyroscope Errors Regardless of Magnetic Perturbation," Sensors 2011, 11, 11390-11414; doi:10.3390/s111211390, 25 pp. published Nov. 30, 2011.
Ainsworth et al., "Simulation Model for Transcervical Laryngeal Injection Providing Real-time Feedback," Annals of Otology, Rhinology & Laryngology, 2014, col. 123 (12), pp. 881-886.
Andraos et al., "Sensing your Orientation" Address 2007, 7 pp.
Arms, S.W., "A Vision for Future Wireless Sensing Systems," 44 pp., 2003.
Banivaheb, Niloofar, "Comparing Measured and Theoretical Target Registration Error of an Optical Tracking System," Feb. 2015, Toronto, Ontario, 128 pp.
Bao, et al., "A Novel Map-Based Dead-Reckoning Algorithm for Indoor Localization", J. Sens. Actuator Networks, 2014, 3, 44-63; doi:10.3390/jsan3010044, 20 pp., Jan. 3, 2014.
Begg et al., "Computational Intelligence for Movement Sciences: Neural Networks and Other Emerging Techniques", *Idea Group Inc (IGI)*, 2006.
Benbasat et al., "An Inertial Measurement Framework for Gesture Recognition and Applications," I. Wachsmuth and T. Sowa (Eds.): GW2001, Springer-Verlag Berlin Heidelberg, 12 pp., 2002.
Bergamini et al., "Estimating Orientation Using Magnetic and Inertial Sensors and Different Sensor Fusion Approaches: Accuracy Assessment in Manual and Locomotion Tasks", Oct. 2014, 18625-18649.
Blum et al., "A Review of Computer-Based Simulators for Ultrasound Training," Society for Simulation in Healthcare, Apr. 2013, vol. 8, pp. 98-108.
Botden et al., "Suturing training in Augmented Reality: gaining proficiency in suturing skills faster," Surg Endosc, 2009, vol. 23, pp. 2131-2137.
Botden et al., "Augmented versus Virtual Reality Laparoscopic Simulation: What Is the Difference?," World J. Surgery, 31, 2007, 10 pp.
Botden et al., "Face validity study of the ProMIS Augmented Reality laparoscopic suturing simulator," Surgical Technology International, Feb. 2008, 17, 16 pp.
Botden et al., "What is going on in augmented reality simulation in laparoscopic surgery," Surgical Endoscopy 23, 2009, 1693-1700.
Bova et al.,"Mixed-Reality Simulation for Neurosurgical Procedures," Neurosurgery, Oct. 2013, vol. 73, No. 4, pp. S138-S145.
Brennan et al., "Classification of diffuse light emission profiles for distinguishing skin layer penetration of a needle-free jet injection," Biomedial Optics Express, Oct. 1, 2019, vol. 10, No. 10, pp. 5081-5092.
Brennan et al., "Light source depth estimation in porcine skin using spatially resolved diffuse imaging," *2016 38th Annual International Conference of the IEEE Engineering in Medicine and Biology Society* (EMBC), Orlando, FL, 2016, pp. 5917-5920.
Brett, et al., "Simulation of resistance forces acting on surgical needles," Proceedings of the Instiutional of Mechanical Engineers Part H Journal of Engineering in Medicine, Feb. 1997, vol. 211 Part H, pp. 335-347.
Brunet et al., "Uncalibrated Stereo Vision," A CS 766 Project, University of Wisconsin—Madison, 6 pp, Fall 2004, http://pages.cs.wisc.edu/~chaol/cs766/.
Brunet et al., "Uncalibrated Stereo Vision," A CS 766 Project, University of Wisconsin—Madison, 13 pp, Fall 2004, http://pages.cs.wisc.edu/~chaol/cs766/.
Buchanan, Judith Ann, "Use of Simulation Technology in Dental Education," Journal of Dental Education, 2001, vol. 65, No. 11, 1225-1231.
CAE Healthcare, "CAE ProMIS Laparoscopic Simulator," Product Brochure/Overview, 2012, 2 pp.
Capsulorhexis forceps only technique rehearsed on EYESi before or (Feb. 10, 2010), https://www.youtube.com/watch?v=ySMI1Vq6Ajw.
Chui et al., "Haptics in computer-mediated simulation: Training in vertebroplasty," Simulation & Gaming, Dec. 2006, vol. 37, No. 4, pp. 438-451.
Comsa et al, "Bioluminescence imaging of point sources implants in small animals post mortem: evaluation of a method for estimating source strength and depth", *Phys. Med. Biol.*, Aug. 2007, vol. 52, No. 17, pp. 5415-5428.
Correa et al., "Virtual Reality Simulator for Dental Anesthesia Training in the Inferior Alveolar Nerve Block," Journal of Applied Oral Science, vol. 25, No. 4, Jul./Aug. 2017, pp. 357-366.
Coquoz et al., "Determination of depth of in vivo bioluminescent signals using spectral imaging techniques," Conference Proceedings of SPIE, 2003, vol. 4967, pp. 37-45, San Jose, CA.
Craig, Alan B., "Augmented Reality Hardware," Understanding Augmented Reality Chapters, 2013, Elsevier Inc., pp. 69-124.
Cumin et al.,"Simulators for use in anaesthesia," Anaesthesia, 2007, vol. 62, pp. 151-162.
Datta et al., "The use of electromagnetic motion tracking analysis to objectively measure open surgical skill in the laboratory-based model". Vol. 193, No. 5, Nov. 2001, pp. 479-485.
Davenar123, DentSim (Mar. 18, 2008), https://www.youtube.com/watch?v=qkzXUHay1W0.
DentSim Educators, DentSim Classroom Introduction (Aug. 8, 2013), https://vimeo.com/79938695.
DentSimLab, Aha Moments—Dentsim Students explain how their dental skills are improving (Nov. 13, 2013), https://www.youtube.com/watch?v=02NgPmhg55Q.
Desjardins, et al. "Epidural needle with embedded optical fibers for spectroscopic differentiation of tissue: ex vivo feasibility study", Biomedical Optics Express, vol. 2(6): pp. 1-10. Jun. 2011.
Dine et al., "Improving cardiopulmonary resuscitation quality and resuscitation training by combining audiovisual feedback and debriefing," Crit Care Med, 2008 vol. 36, No. 10, pp. 2817-2822.
EPED Taiwan, EPED—Computerized Dental Simulator (CDS-100) (Jun. 9, 2014), https://www.youtube.com/watch?v=m8UXaV2ZSXQ.
"EPGL Medical Invents Smart Epidural Needle, Nerve Ablation And Trigger Point Treatment Devices: New Smart Medical Devices Will Give Physicians Advanced Situational Awareness During Critical Procedures," EPGL Medical, dated Aug. 12, 2013, in 3 pages. Retrieved from http://www.prnewswire.com/news-releases/epgl-medical-invents-smart-epidural-needle-nerve-ablation-and-trigger-point-treatment-devices-219344621.html#.
"The EpiAccess System: Access with Confidence", EpiEP Epicardial Solutions, dated 2015, in 2 pages.
Esteve, Eric, "Why do you need 9D Sensor Fusion to support 3D orientation?", 5 pp., Aug. 23, 2014, https://www.semiwiki.com/forum/content/3794-why-do-you-need-9d-sensor-fusion-support-3d-orientation.html.
Ford et al.,"Impact of simulation-based learning on mediation error rates in critically ill patients," Intensive Care Med, 2010, vol. 36, pp. 1526-1531.
Franz et al., "Electromagnetic Tracking in Medicine—A Review of Technology, Validation, and Applications," IEEE, Transactions on Medical Imaging, Aug. 2014, vol. 33, No. 8, pp. 1702-1725.

(56) References Cited

OTHER PUBLICATIONS

Garg et al., "Radial Artery cannulation—Prevention of pain and Techniques of cannulation: review of literature," The Internet Journal of Anesthesiology, vol. 19, No. 1, 2008, in 6 pages.
Garrett et al., "High-Fidelity Patient Simulation: Considerations for Effective Learning," Teaching with Technoloyg: High-Fidelity Simulation, 2010, vol. 31, No. 5, pp. 309-313.
Gottlieb et al., "Faculty Impressions of Dental Students' Performance With and Without Virtual Reality Simulation,"Journal of Dental Education, 2011, vol. 75, No. 11, pp. 1443-1451.
Gottlieb et al., "Simulation in Dentistry and Oral Health," The Comprehensive Textbook of Healthcare Simulation Chapter 21, Apr. 2013, pp. 329-340.
Grenet et al., "spaceCoder: a Nanometric 3D Position Sensing Device," CSEM Scientific & Technical Report, 1 page, 2011.
Helen, L., et al. "Investigation of tissue bioimpedance using a macro-needle with a potential application in determination of needle-to-nerve proximity", Proceedings of the 8th International Conference on Sensing Technology, Sep. 2-4, 2014, pp. 376-380.
Hoffman et al., "Arytenoid Repositioning Device," Annals of Otology, Rhinology & Laryngology, 2014, vol. 123 (3); pp. 195-205.
Hoffman et al., "Transillumination for Needle Localization in the Larynx," The Laryngoscope, 2015, vol. 125, pp. 2341-2348.
Hotraphinyo et al., "Precision measurement for microsurgical instrument evaluation", *Conference Proceedings of the 23rd Annual International Conference of the IEEE Engineering in Medicine and Biology Society*, 2001, vol. 4, pp. 3454-3457.
Huang et al., "CatAR: A Novel Stereoscopic Augmented Reality Cataract Surgery Training System with Dexterous Instrument Tracking Technology," CHI' 18: Proceedings of the 2018 CHI Conference on Human Factors in Computing Systems, Apr. 21-26, 2018, pp. 1-12, ACM, Montreal, Canada.
Image Navigation, DentSim by Image Navigation—Augmented Reality Dental Simulation, Nov. 2014, 5 pp., available at https://image-navigation.com/wp-content/uploads/2014/11/DentSim-V5-2-Pager.pdf.
Image Navigation, DentSim Computerized Dental Training Simulator, Product Brochure, Jul. 2014, available at https://image-navigation.com/wp- content/uploads/2014/07/DentsimBrochure.pdf.
Inition. Virtual Botox: Haptic App Simulated Injecting The Real Thing. Retrieved from http://inition.co.uk/case-study/virtual-botox-haptic-app-simulates-injecting-real-thing., printed on Oct. 30, 2013 in 2 pgs.
International Search Report and Written Opinion for Appl. No. PCT/US2013/067352 dated Mar. 31, 2014 in 10 pages.
International Search Report and Written Opinion for Appl. No. PCT/US2015/011845, dated Apr. 29, 2015 in 10 pages.
International Search Report and Written Opinion for Appl. No. PCT/US2015/019974, dated May 21, 2015, 10 pages.
International Search Report and Written Opinion for Appl. No. PCT/US2015/062798, dated Mar. 14, 2016, 12 pages.
International Search Report and Written Opinion for Appl. No. PCT/US2017/020509, dated Jul. 13, 2017, 24 pages.
Invensense, Inc., "MPU-9150 EV Board User Guide," May 11, 2011, pp. 1-15.
Invensense, Inc., "MPU-9150 Product Specification Revision 4.3," Sep. 18, 2013, pp. 1-50.
Invensense, Inc., "MPU-9150 Register Map and Descriptions Revision 4.2," Sep. 18, 2013, pp. 1-52.
Jafarzadeh et al., "Design and construction of an automatic syringe injection pump," Pacific Science Review A: Natural Science and Engineering 18, 2016, in 6 pages.
Jasinevicius et al., "An Evaluation of Two Dental Simulation Systems: Virtual Reality versus Contemporary Non-Computer-Assisted," Journal of Dental Education, 2004, vol. 68, No. 11, 1151-1162.
Joint Claim Construction Chart, filed on Mar. 18, 2020 in 8 pages.

Kalvøy, H., et al., "Detection of intraneural needle-placement with multiple frequency bioimpedance monitoring: a novel method", Journal of Clinical Monitoring and Computing, Apr. 2016, 30(2):185-192.
Kandani et al., "Development in blood vessel searching system for HMS," SPIE, Infrared Systems and PhotoelectronicTehcnology III, 2008, vol. 7065, pp. 1-10.
Kettenbach et al., "A robotic needle-positioning and guidance system for CT-guided puncture: Ex vivo results," Minimally Invasive Therapy and Allied Technologies, vol. 23, 2014, in 8 pages.
Khosravi, Sara, "Camera-Based Estimation of Needle Pose for Ultrasound Percutaneous Procedures," University of British Columbia, 2008, pp. ii-83.
Krupa et al., "Autonomous 3-D positioning of surgical instruments in robotized laparoscopic surgery using visual servoing", *IEEE Trans. Robotics and Automation*, 2003, vol. 19, pp. 842-853.
Kumar et al., "Virtual Instrumentation System With Real-Time Visual Feedback and Needle Position Warning Suitable for Ophthalmic Anesthesia Training," IEEE: Transactions on Instrumentation and Measurement, May 2018, vol. 67, No. 5, pp. 1111-1123.
Lacey et al., "Mixed-Reality Simulation of Minimally Invasive Surgeries," IEEE Computer Society, 2007, pp. 76-87.
Ladjal, et al., "Interactive Cell Injection Simulation Based on 3D Biomechanical Tensegrity Model," 2008 IEEE/RSJ International Conference on Intelligent Robots and Systems, in 9 pages.
Laerdal, "Virtual Phlebotomy—Directions for Use," Self-directed Phlebotomy learning, Aug. 4, 2020, pp. 1-100.
Laerdal Medical, http://www.laerdal.com/us/nav/203/Venous-Arterial-Access, printed Mar. 8, 2019 in 3 pgs.
Lampotang et al.,"A Subset of Mixed Simulations: Augmented Physical Simulations with Virtual Underlays," Interservice/Idnustry Training, Simualtion, and Education Conference (I/ITSEC), 2012, pp. 1-11.
Lampotang et al., "Mixed Reality Simulation for Training Reservists and Military Medical Personnel in Subclavian Central Venous Access," Informational Poster, Ufhealth, Center for Safety, Simulation and Advanced Learning Technologies, 2015, 1 pp. available at https://simulation.health.ufl.edu/files/2018/12/Dept_CoR_2015-Mixed_Reality_Simulation_for_Training.pdf.
Lee et al., "A Phantom Study on the Propagation of NIR Rays under the Skin for Designing a Novel Vein-Visualizing Device," ICCAS, Oct. 20-23, 2013, pp. 821-823.
Lee et al., "An Intravenous Injection Simulator Using Augmented Reality for Veterinary Education and its Evaluation," Proceedings of the 11th ACM SIGGRAPH International Conference on Virtual-Reality Continuum and its Applications in Industry, Dec. 2-4, 2012, in 4 pages.
Lee et al., "Augmented reality intravenous injection simulator based 3D medical imaging for veterinary medicine," The Veterinary Journal, 2013, vol. 196, No. 2, pp. 197-202.
Lee et al., "The utility of endovascular simulation to improve technical performance and stimulate continued interest of preclinical medical students in vascular surgery," Journal of Surgical Education, 2009 APDS Spring Meeting, vol. 66, No. 6, 367-373.
Lee et al., "Virtual Reality Ophthalmic Surgical Simulation as a Feasible Training and Assessment Tool: Results of a Multicentre Study," Canada Journal of Ophthalmology, Feb. 2011 Vol. 46, No. 1, 56-60.
Lemole et al., "Virtual Reality in Neurosurgical Education: Part-Task Ventriculostomy Simulation with Dynamic Visual and Haptic Feedback," Neurosurgery, Jul. 2007, vol. 61, No. 1, pp. 142-149.
Leopaldi et al., "The dynamic cardiac biosimulator: A method for training physicians in beating-heart mitral valve repair procedures," The Journal of Thoracic and Cardiovascular Surgery, 2018, vol. 155, No. 1, pp. 147-155.
Lim, M.W. et al., "Use of three-dimensional animation for regional anaesthesia teaching: application to interscalene brachial plexus blockade," British Journal of Anaesthesia, Advance Access, 2004, vol. 94, pp. 372-377.
Liu et al. "Robust Real-Time Localization of Surgical Instruments in the Eye Surgery Stimulator (EyeSi)", *Signal and Image Processing*, 2002.

(56) References Cited

OTHER PUBLICATIONS

Liu et al. "Study on an Experimental AC Electromagnetic Tracking System" Proceedings of the 5th World Congress on Intelligent Control and Automation, Jun. 15-19, 2001. pp 3692-3695.
Madgwick, Sebastian O.H., "An efficient orientation filter for inertial and inertial/magnetic sensor arrays," 32 pp., Apr. 30, 2010.
Medgadget Editors, "EYESI Surgical Simulator," Medgadget, Aug. 28, 2006,4 pp., printed on Feb. 7, 2020, https://www.medgadget.com/2006/08/eyes_i_surgical.html.
Merlone1, Eyesi_Cataract_2011 (Sep. 9, 2011), https://www.youtube.com/watch?v=XTulabWmEvk.
Merril et al., "The Ophthalmic Retrobulbar Injection Simulator (ORIS): An Application of Virtual Reality to Medical Education", *Proc. Ann. Symp. Comput. Med. Care*, 1992, pp. 702-706.
Microsoft, "Integrating Motion and Orientation Sensors," 85 pp., Jun. 10, 2013.
Miller, Nathan L., Low-Power, Miniature Inertial Navigation System with Embedded GPS and Extended Kalman Filter, MicroStrain, Inc., 12 pp., 2012.
MPU-9150 9-Axis Evaluation Board User Guide, Revision 1.0, 15 pp., May 11, 2011, http//www.invensense.com.
MPU-9150, Register Map and Descriptions, Revision 4.2, 52 pp., Sep. 18, 2013, http//www.invensense.com.
MPU-9150, Product Specification, Revision 4.3, 50 pp., Sep. 18, 2013, http//www.invensense.com.
Mukherjee et al., "A Hall Effect Sensor Based Syringe Injection Rate Detector", *IEEE 2012 Sixth Int'l Conf. on Sensing Technol. (ICST)*, Dec. 18-21, 2012.
Mukherjee et al., "An Ophthalmic Anesthesia Training System Using Integrated Capacitive and Hall Effect Sensors," IEEE, Transactions on Instrumentation and Measurement, Jan. 2014, vol. 63, No. 5 , 11 pp.
Nelson, Douglas A. Jr., "A Modular and Extensible Architecture Integrating Sensors, Dynamic Displays of Anatomy and Physiology, and Automated Instruction for Innovations in Clinical Education" Doctoral Dissertation, Univ. of Pitt., 2017, 260 pp.
Nelson et al., "The Tool Positioning Tutor: A Target-Pose Tracking and Display System for Learning Correct Placement of a Medical Device," *Medicine Meets Virtual Reality* 18, IOS Press, 2011, 5 pp.
Ottensmeyer et al., "Ocular and Craniofacial Trauma Treatment Training System: Overview & Eyelid Laceration Module," workshop Proceedings of the 8th International Conference on Intelligent Environments, IOS Press, 2012, 13 pp.
Ozturk wt al.,"Complications Following Injection of Soft-Tissue Fillers," Aesthetic Surgery Journal, from the American Society for Aesthetic Plastic Surgery, Inc. Reprints and permissions, http://www.sagepub.com/journalsPermissions.nav, Aug. 2013, pp. 862-877.
Petition for Inter Partes Review of U.S. Pat. No. 9,792,836, Pursuant to 35 U.S.C. §§ 311-19, 37 C.F.R. § 42.100 ET SEQ., IPR2020-00042, dated Oct. 11, 2019.
Petition for Inter Partes Review of U.S. Pat. No. 10,290,231, Pursuant to 35 U.S.C. §§ 311-19, 37 C.F.R. § 42.100 ET SEQ., IPR2020-00935 dated May 13, 2020.
Petition for Inter Partes Review of U.S. Pat. No. 10,290,232, Pursuant to 35 U.S.C. §§ 311-19, 37 C.F.R. § 42.100 ET SEQ., IPR2020-00937 dated May 13, 2020.
Patterson et al., "Absorption spectroscopy in tissue-simulating materials: a theoretical and experimental study of photon paths", Appl. Optics, Jan. 1995, vol. 34, No. 1, pp. 22-30.
Pitt Innovates, BodyExplorer™ (Sep. 24, 2014), https://www.youtube.com/watch?v=T6G2OWJm5hs.
Pitt Innovates, Pitt Student Innovator Award, Pitt Intellectual Property 2017, Douglas A Nelson Jr. (Nov. 28, 2017), https://www.youtube.com/watch?v=0_CVBgWtCLo.
Poyade et al., "Development of a Haptic Training Simulation for the Administration of Dental Anesthesia Based Upon Accurate Anatomical Data," Conference and Exhibition of the European Association of Virtual and Augmented Reality, 2014, in 5 pages.
PST Iris Tracker, Plug and Play, 3D optical motion tracking specifications, 1 p., Dec. 4, 2014, www.pstech.com.
PST Iris Tracker, Instruction Manual, 3D optical motion tracking specifications, 42 pp., Jul. 27, 2012, www.pstech.com.
Quio, "Smartinjector," available at https://web.archive.org/web/20161017192142/http://www.quio.com/smartinjector, Applicant believes to be available as early as Oct. 17, 2016, in 3 pages.
Rahman et al., "Tracking Manikin Tracheal Intubation Using Motion Analysis," Pediatric Emergency Care, Aug. 2011, vol. 27, No. 8, pp. 701-705.
Robinson et al., "A Mixed-Reality Part-Task Trainer for Subclavian Venous Access," Journal of the Society for Simulation in Healthcare, Feb. 2014, vol. 9, No. 1, pp. 56-64.
Salem et al., "Clinical Skills Laboratories "CSLs" Manual 1432-2011," Jan. 2011, pp. 0-88.
Samosky et al., "BodyWindows: Enhancing a Mannequin with Projective Augmented Reality for Exploring Anatomy, Physiology and Medical Procedures," Medicine Meets Virtual Reality 19, 2012, 433, J.D. Westwood et al. eds., IOS Press, pp. 433-439.
Samosky et al., "Enhancing Medical Device Training with Hybrid Physical—Virtual Simulators: Smart Peripherals for Virtual Devices," Medicine Meets Virtual Reality 20, Jan. 2013, J.D. Westwood et al. eds., IOS Press 377, pp. 377-379.
Samosky, Joseph, "View from the Top: Simulation Director Envisions Greater Use For Training Tool," Biomedical Instrumentation & Technology, 2012, pp. 283-288.
Samosky et al.,"Toward a Comprehensive Hybrid Physical—Virtual Reality Simulator of Peripheral Anesthesia with Ultrasound and Neurostimulator Guidance," Medicine Virtual Reality 18, IOS Press, 2011, pp. 552-554.
Satava, "Accomplishments and Challenges of Surgical Simulation", Dawning of the next-generation surgical education, Surgical Endoscopy Ultrasound and Interventional Techniques, Online publication, Feb. 6, 2001, in 10 pages.
Schneider, Chad Michael, "Systems for Robotic Needle Insertion and Tool-Tissue Interaction Modeling," Research Gate, 2004, pp. 1-74, Baltimore, Maryland.
Simbionix, Valencia College's CVT program uses Simbionix ANGIO Mentor simulators, Feb. 26, 2013, https://www.youtube.com/watch?v=oAE0fWzXMjw.
SimEx, "Dental Augmented Reality Simulator," EPED, 3 pp. https://www.epedmed.com/simex. Available as early as 2019.
Spiteri et al., "Phacoemulsification Skills Training and Assessment," The British Journal of Ophthalmology 2010, Aug. 2009, 20 pp.
State Electronics, "Sensofoil Membrane Potentiometer," Product Information and Technical Specifications, received on May 15, 2020 in 6 pages.
Struik, Pieter, "Ultra Low-Power 9D Fusion Implementation: A Case Study," Synopsis, Inc., 7 pp., Jun. 2014.
Stunt et al., "Validation of ArthroS virtual reality simulator for arthroscopic skills," Knee Surgery Sports Traum. Arthroscopy 23, Jun. 11, 2014, 8 pp.
Sultan et al.,"A Novel Phantom for Teaching and Learning Ultrasound-guided Needle Manipulation," Journal of Medical Ultrasound, Elsevier Taiwan LLC, Jul. 2013, vol. 21, pp. 152-155.
Sutherland, et al. "An Augmented Reality Haptic Training Simulator for Spinal Needle Procedures," IEEE, 2011.
Suzuki et al., "Simulation of Endovascular Neurointervention Using Silicone Models: Imaging and Manipulation," Neurol Med Chir (Tokyo), 2005, vol. 45, pp. 567-573.
The Simulation Group, Internet Archive Wayback webpage capture of http://www.medicalsim.org/virgil.htm, apparently available Apr. 10, 2013, site visited Aug. 25, 2020.
The Simulation Group, Virgil™ Videos (2002), http://www.medicalsim.org/virgil_vid.htm; http://www.medicalsim.org/virgil/virgil%20expert.mpg.
Ting et al., "A New Technique to Assist Epidural Needle Placement: Fiberoptic-guided Insertion Using Two Wavelengths," Anesthesiology, 2010, vol. 112, pp. 1128-1135.
Touch of Life Technologies, "ToLTech Cystoscopy Simulator Helps Practice BOTOX Injections," https://www.medgadget.com/2012/05/

(56) References Cited

OTHER PUBLICATIONS toltech-cystoscopy-simulator-helps-practice-botox-injections.html, May 2012, printed on Feb. 6, 2020 in 2 pgs.
Touch of Life Technologies, "Touch of Life Technologies' new cystoscopy and bladder injection simulator offers urologists training on use of BOTOX®," https://www.urotoday.com/recent-abstracts/pelvic-health-reconstruction/urinary-incontinence/50289-touch-of-life-technologies-new-cystoscopy-and-bladder-injection-simulator-offers-urologists-training-on-use-of-botox-onabotulinumtoxina-as-treatment-for-urinary-incontinence-in-adults-with-neurological-conditions.html, May 2012, printed on Feb. 6, 2020 in 2 pgs.
Truinject Corp., "Smart Injection Platform," http://truinject.com/technology/, printed Jan. 13, 2018, in 3 pages.
Ufcssalt, "Video of mixed simulation for placement of CVL needle"—(Patent Pending), Dec. 5, 2011, https://www.youtube.com/watch?v=0ITIFbiiwRs.
UFhealth, "UF developing mixed-reality simulators for training in treatment of injured soldiers," Aug. 20, 2014, https://www.youtube.com/watch?v=sMxH11prc10& feature=emb_title.
Ungi et al., "Perk Tutor: An Open-Source Training Platform for Ultrasound-Guided Needle Insertions," IEEE Transactions on Biomedical Engineering, Dec. 2012, vol. 59, No. 12, pp. 3475-3481.
Univervisty of Pittsburgh Innovation Institute, "BodyExplorer: An Automated Augmented Reality Simulator for Medical Training and Competency Assessment," Mar. 2016, 2 pp.
Univervisty of Pittsburgh Innovation Institute, "BodyExplorer: Enhancing a Mannequin Medical Simulator with Sensing. Tangible Interaction and Projective Augmented Reality for Exploring Dynamic Anatomy, Physiology and Clinical Procedures," 2012, pp. 1-3.
Van Sickle et al., "Construct validation of the ProMIS simulator using novel laparoscopic suturing task", *Surg Endosc*, Sep. 2005, vol. 19, No. 9, pp. 1227-1231.
Varesano, Fabio, "Prototyping Orientation and Motion Sensing Objects with Open Hardware," Dipartimento di Informatica, Univ. Torino, http://www.di.unito.it/~varesano, Feb. 10, 2013, 4 pp.
Varesano, Fabio, "FreeIMU: An Open Hardware Framework for Orientation and Motion Sensing," Dipartimento di Informatica, Univ. Torino, http://www.di.unito.it/~varesano, Mar. 20, 2013, 10 pp.
Vaughan et al., "A review of virtual reality based training simulators for orthopedic surgery," Journal Engineering and Physics, 2016, vol. 38, Elsevier Ltd., pp. 59-71.
Virgil™, The Simulation Group/CIMIT, "Medical Simulation Chest Trauma Training System," 2002, 6 pp. http://www.medicalsim.org/virgil.htm.
VirtaMed ArthroS™, "Virtual reality arthroscopy for knee, shoulder, hip, ankle & Fast basic skills," Fact Sheet/Brochure Jul. 13, 2011.
VirtaMed ArthroS™ Module Descriptions. 2019.
VirtaMed, ArthroS—The 2012 Arthroscopic Simulator for Knee Arthroscopy, Feb. 1, 2012, https://www.youtube.com/watch?v=Y6w3AGfAqKA.
VirtaMed, Arthroscopy Training Simulator ArthroS Now With Shoulder Module!, Mar. 13, 2013, https://www.youtube.com/watch?v=kPuAm0MIYg0.
VirtaMed, Arthroscopy Training 2013: VirtaMed ArthroS Shoulder Simulator, Sep. 24, 2013, https://www.youtube.com/watch?v=WdCtPYr0wK0.
Virtamed News, "VirtaMed ArthroS—Virtual reality training for knee arthroscopy," VirtaMed, Jul. 13, 2011, 2 pp. accessed on Feb. 6, 2020,https://www.virtamed.com/en/news/virtamed-arthros-virtual-reality-training-knee-arthroscopy/.
VirtaMed, VirtaMed ArthroS™—diagnostic and therapeutic arthroscopy in both the knee and shoulder (Apr. 15, 2014), https://www.youtube.com/watch?v=gtklSWnOzRc.
Vrmagic,"eyesi by VRmagic Surgical Simulator," Product Brochure, 2015, available at https://pdf.medicalexpo.com/pdf/vrmagic/eyesi-surgical-product-brochure/112458- 159450.html.

Walsh et al., "Use of Simulated Learning Environments in Dentistry and Oral Health Curricula," SLE in Dentistry and Oral Health: Final Report, 2010, Health Workforce Australia, pp. 1-112.
Welk et al., "DentSim—A Future Teaching Option for Dentists," 7 International Journal of Computerized Dentistry, 2004, 9 pp.
Wik et al., "Intubation with laryngoscope versus transillumination performed by paramedic students on manikins and cadavers", *Resuscitation*, Jan. 1997, vol. 33, No. 3, pp. 215-218.
Wiles, Andrew et al., "Accuracy assessment and interpretation for optical tracking systems," SPIE, Medical Imaging: Visualization, Image-Guided Procedures and Display, 2004, vol. 5367, pp. 1-12.
Yeo et al., "The Effect of Augmented Reality Training on Percutaneous Needle Placement in Spinal Facet Joint Injections," IEEE, Transactions on Biomedical Engineering, Jul. 2011, vol. 58, No. 7, 8 pp.
Yu et al., "Development of an In Vitro Tracking System with Poly (vinyl alcohol) Hydrogel for Catheter Motion," Journal of Biomedical Science and Engineering, 2010, vol. 5, No. 1, 11-17.
Blue Telescope, Daisey Injector Simulator, Available athttps://www.bluetelescope.com/work/ipsen-injection-simulator. Blue Telescope Laboratories 2020, site visited Aug. 24, 2020.
IDA Design Awards—Winners, Daisey Injection Simulator, available at https://idesignawards.com/winners/zoom.php?eid=9-11737-16&count=0&mode=, Available as early as Sep. 7, 2016.
Mnemonic, Ipsen Injection Simulators, available at http://mnemonic.studio/project/ispen-injection-simulators. Copyright 2019, Website viewed on Aug. 24, 2020.
Mnemonic, Injection Simulator (Oct. 20, 2017), https://vimeo.com/239061418.
Association of American Medical Colleges, Medical Simulation in Medical Education: Results of an AAMC Survey (Sep. 2011) ("AAMC Survey"), in 48 pages.
"A Virtual Reality Based Joint Injection Simulator Phase III", https://www.sbir.gov/. Retreived Mar. 5, 2021, in 2 pages.
"B-Smart disposable manometer for measuring peripheral nerve block injection pressures", B. Braun USA, 2016, in 4 pages.
Berkelman et al., "Co-Located 3D Graphic and Haptic Display using Electromagnetic Levitation", The Institute of Electrical and Electronics Engineers, 2012 in 6 pages.
J. Clark et al., A quantitative scale to define endoscopic torque control during natural orifice surgery, 22 Minimally Invasive Therapy & Allied Technologies 17-25 (2013).
Coles et al., "Modification of Commercial Force Feedback Hardware for Needle Insertion Simulation", Studies in Health Technology and Informatics, 2011 in 1 page.
Dang et al., "Development and Evaluation of an Epidural Injection Simulator with Force Feedback for Medical Training", Studies in Health Technology and Informatics, 2001, vol. 81., pp. 97-102.
A. D'Angelo et al., Use of decision-based simulations to assess resident readiness for operative independence, 209 Am J Surg. 132-39 (2015).
V. Datta et al., The relationship between motion analysis and surgical technical assessments, 184(1) Am J Surg.70-73 (2002).
Decision Denying Institution of Inter Parties Review for IPRP2020-00042, U.S. Pat. No. 9792836, dated Apr. 14, 2020, in 20 pages.
Defendant SHDS, Inc.'s(F/K/A Nestle Skin Health, Inc.) Supplemental Disclosure of Invalidity Contentions, Case No. 1:19-cv-00592-LPS-JLH, *Truinject Corp., v. Galderma, S.A., Galderma Laboratories, L.P., Nestle Skin Health, Inc.*, dated Aug. 3, 2020, in 6 pages.
Defendant SHDS, Inc.'s(F/K/A Nestle Skin Health, Inc.) Disclosure of Preliminary Invalidity Contentions, Case No. 1:19-cv-00592-LPS-JLH, *Truinject Corp., v. Galderma, S.A., Galderma Laboratories, L.P., Nestle Skin Health, Inc.*, dated Feb. 12, 2020, in 136 pages.
Defendant SHDS, Inc.'s(F/K/A Nestle Skin Health, Inc.) Second Supplemental Disclosure of Invalidity Contentions, Case No. 1:19-cv-00592-LPS-JLH, *Truinject Corp., v. Galderma, S.A., Galderma Laboratories, L.P., Nestle Skin Health, Inc.*, dated Mar. 5, 2021, in 9 pages.
Defendant SHDS, Inc.'s(F/K/A Nestle Skin Health, Inc.) Final Invalidity Contentions, Case No. 1:19-cv-00592-LPS-JLH, *Truinject*

(56) References Cited

OTHER PUBLICATIONS

*Corp., v. Galderma, S.A., Galderma Laboratories, L.P., Nestle Skin Health, Inc.*, dated Jun. 18, 2021, in 54 pages.
A. Dosis et al., Synchronized Video and Motion Analysis for the Assessment of Procedures in the Operating Theater, 140 Arch Surg. 293-99 (2005).
Färber et al., "Needle Bending in a VR-Puncture Training System Using a 6DOF Haptic Device", Studies in Health Technology and Informatics, 2009, vol. 142, in 3 pages.
Gobbetti et al., "Catheter Insertion Simulation with co-registered Direct Volume Rendering and Haptic Feedback", Studies in Health Technology and Informatics, vol. 70, 2000 in 3 pages.
"Immersion Medical Joins with PICC Excellence to Promote Training Products for Peripherally Inserted Central Catheter Procedure", Immersion Corporation, Business Wire 2006. Dated Jan. 9, 2006, in 3 pages.
"Immersion Medical Upgrades CathSim AccuTouch", Med Device Online, dated Jan. 12, 2005 in 1 page.
Judgment and Final Written Decision Determing All Challenged Claims Unpatentable, U.S. Pat. No. 10,290,231 B2, IPR2020-00935.
Judgment and Final Written Decision Determing All Challenged Claims Unpatentable, U.S. Pat. No. 10,290,232 B2, IPR2020-00937.
Laerdal, "Virtual I.V.—Directions for Use", www.laerdal.com, dated Sept. 3, 2010, in 100 pages.
Laerdal, "Virtual I.V. Sell Sheet", www.laerdal.com, dated Mar. 26, 2013, in 2 pages.
Laerdal, "Virtual I.V. Simulator (Discontinued)", www.laerdal.com, in 5 pages. Retrieved Jul. 23, 2021.
Lance Baily, Polhemus Delivers World Class Motion Tracking Technology to Medical Simulation Industry, healthysimulation.com,(May 2,2016),https://www.healthysimulation.com/8621/polhemus-deliversworld-class-motion-tracking-technology-to-medical-simulationindustry/.
S. Laufer et al., Sensor Technology in Assessments of Clinical Skill, 372 N Engl Jmed 784-86 (2015).
"Learning by Feel: ToLTech and Allergan Simulator", 3D Systems, dated May 8, 2012, in 93 pages.
Lee et al., "Evaluation of the Mediseus® Epidural Simulator", Anaesthesia and Intensive Care (2012), vol. 40, No. 2, pp. 311-318.
Lendvay et al., "The Biomechanics of Percutaneous Needle Insertion", Studies in Health Technology and Informatics, Jan. 2008 in 2 pages.
Lim et al., "Simulation-Based Military Regional Anesthesia Training System", US Army Medical Research and Materiel Command Fort Detrick MD, Telemedicine and Advanced Technology Research Center, 2008, in 8 pages.
Luboz et al., "ImaGiNe Seldinger: First simulator for Seldinger technique and angiography training", Computer Methods and Programs in Biomedicine, vol. 111, No. 2, Aug. 2013 pp. 419-434.
Mastmeyer et al., "Direct Haptic Voluming Rendering in Lumbar Puncture Simulation", Studies in Health Technology and Informatics, vol. 173, No. 280, 2012 in 8 pages.

Mastmeyer et al., "Real-Time Ultrasound Simulation for Training of US-Guided Needle Insertin in Breathing Virtual Patients", Studies in Health Technology and Informatics, Jan. 2016 in 9 pages.
Medgadget Editors, "ToLTech Cystoscopy Simulator Helps Practice BOTOX Injections", Medgadget, May 14, 2012, in 2 pages. Printed on Feb. 6, 2020, http://www.medgadget.com/2012/05/toltech-cystoscopy-simulator-helps-practice-botox-injections.html.
K. Perrone et al., Translating motion tracking data into resident feedback: An opportunity for streamlined video coaching, 209 Am J Surg. 552-56 (2015).
Petition for Inter Partes Review of U.S. Pat. No. 9,792,836, Pursuant to 35 U.S.C. §§ 311-19, 37 C.F.R. § 42.100 ET SEQ., IPR2020-00042, dated Oct. 17, 2017.
C. Pugh et al., A Retrospective Review of TATRC Funding for Medical Modeling and Simulation Technologies, 6 Simulation in Healthcare, 218-25 (2011).
Petition for Inter Partes Review of U.S. Pat. No. 10,290,232, Pursuant to 35 U.S.C. §§ 311-19, 37 C.F.R. § 42.100 ET SEQ., IPR2020-00937 dated May 14, 2019.
Petition for Inter Partes Review of U.S. Pat. No. 10,290,231, Pursuant to 35 U.S.C. §§ 311-19, 37 C.F.R. § 42.100 ET SEQ., IPR2020-00935 dated May 14, 2019.
Report and Recommendation, Case No. 19-592-LPS-JLH, *Truinject Corp., v. Galderma, S.A., Galderma Laboratories, L.P., Nestle Skin Health, Inc.*, dated Jun. 18, 2020, in 18 pages.
Sclaverano et al. "BioSym : a simulator for enhanced learning of ultrasound-guided prostate biopsy", Studies in Health Technology and Informatics, 2009 in 6 pages.
S. Shaharan et al., Motion Tracking System in Surgical Training, 2017 Intechopen 3-23 (2017), available at http://dx.doi.org/10.5772/intechopen.68850.
Shen et al., "Virtual trainer for intra-destrusor injection of botulinum toxin to treat urinary incontinence", Studies in Health Technology and Informatics, vol. 173, 2012 in 4 pages.
J. Šilar et al., Development of In-Browser Simulators for Medical Education: Introduction of a Novel Software Toolchain, 21 J Med Internet Res. e14160 (published online Jul. 3, 2019).
Vidal et al., "Developing An Immersive Ultrasound Guided Needle Puncture Simulator", Studies in Health Technology and Informatics, 2009, pp. 398-400.
Virtual I.V.® Simulator—1. Introduction. YouTube, uploaded by Laerdal Medical AS, Jan. 19, 2011, www.youtube.com/watch?v=H9Qd6N9vG_A, viewed on Jul. 27, 2021.
Virtual I.V.® Simulator—2. System Overview. YouTube, uploaded by Laerdal Medical AS, Jan. 19, 2011, www.youtube.com/watch?v=l01UFNFU3cU, viewed on Jul. 28, 2021.
Virtual I.V.® Simulator—3. Training overview. YouTube, uploaded by Laerdal Medical AS, Jan. 19, 2011, www.youtube.com/watch?v=5Ut6YkDaNWI, viewed on Jul. 27, 2021.
Wandell et al., "Using a Virtual Reality Simulator in Phlebotomy Training", LabMedicine, (Aug. 2010) vol. 41, No. 8, in 4 pages.
Wolpert et al., "ENISS: An Epidural Needle Insertion Simulation System", Institute of Electrical and Electronics Engineers Inc., 2007 pp. 271-272.

* cited by examiner

SENSORY ENHANCED ENVIRONMENTS FOR INJECTION AID AND SOCIAL TRAINING

INCORPORATION BY REFERENCE

This application is a continuation of U.S. patent application Ser. No. 15/448,364, filed Mar. 2, 2017, entitled "SENSORY ENHANCED ENVIRONMENTS FOR INJECTION AID AND SOCIAL TRAINING", now U.S. Pat. No. 10,849,688, which claims benefit of U.S. Provisional Patent Application No. 62/302,646, filed Mar. 2, 2016 and entitled "SENSORY ENHANCED ENVIRONMENTS FOR INJECTION TRAINING," and U.S. Provisional Patent Application No. 62/399,252, filed Sep. 23, 2016 and entitled "SENSORY ENHANCED ENVIRONMENTS FOR INJECTION TRAINING," the entirety of both of which are hereby incorporated by reference and made party of this specification as if set forth fully herein in its entirety.

FIELD OF THE DISCLOSURE

The present disclosure generally relates to a virtual reality and/or augmented system for providing aid to a physician or healthcare professional during injection procedures and/or for providing social training.

BACKGROUND

A sensory immersive environment, which can also be referred to as a virtual environment, comprises a computer-based or computer-enhanced experience that can simulate for the user a physical presence in places and circumstances that correspond to real or imagined environments. Frequently the experience provided by a virtual environment is interactive, allowing the user to engage and affect the environment. Typically sensory immersive environments are displayed on a screen or through a stereoscopic display worn by the user. Some simulations include additional sensory information such as, for example, sound delivered through speakers or headphones, and tactile information delivered through the use of input and feedback devices. Input devices can include standard devices, such as a keyboard, a mouse, a game controller, etc., or customized, multimodal devices such as a wired glove, an injection tool, or an injection apparatus. More advanced virtual environments can include deeper sensory experiences such as virtual taste, smell, and motion in addition to sight, sound, and touch, enabling participants to interact realistically with the virtual environment. The simulated environment can be similar to the real world to create a lifelike experience, or it can differ significantly from circumstances in the physical world.

A sensory immersive environment may be utilized as an aid to individuals in a variety of situations by providing additional information to the user when the user enters a particular environment. For example, a sensory immersive environment can function as an aid during a variety of medical injection procedures and/or provide educational and training features for health-care professionals performing the medical injection procedures. A variety of medical injection procedures are often performed in prophylactic, curative, therapeutic, or cosmetic treatments. Injections are not limited to treating medical conditions, but may be expanded to treating aesthetic imperfections, restorative cosmetic procedures, procedures for treating migraine, depression, epidurals, orthopedic procedures, self-administered injections, in vitro procedures, or other therapeutic procedures. By way of another example, a sensory immersive environment can similarly function as a social aid for individuals with difficulty recognizing social cues.

SUMMARY

There are numerous advantages to be gained through the use of virtual environments for the aid and training of health-care professionals. A sensory immersive environment provides the user with additional information that allows the user to increase the effectiveness of therapeutic procedures. The sensory immersive environment may provide an opportunity to learn through personal, participatory experience, a modality that is recognized as an effective way for humans to gain and retain a deep understanding of subject matter as well as physical and mental processes. In contrast to the passive, traditional, out-of-context training modes of attending a lecture and reading a text, a virtual environment-based training experience places the trainee in the context and environment of the subject being learned, and it demands active engagement by the trainee to invest mental and physical effort to construct and develop conceptual models of the material being taught. Moreover, immersion in a virtual environment can allow the health-care professional and/or trainee to develop an understanding of the subject matter through physical interaction including manipulation of objects, a central aspect to the process by which humans learn. Virtual environments provide advanced techniques for visualization of subject matter as well, which can enable the health-care professional and/or trainee to sometimes perceive that which is imperceptible. For example, abstract notions such as biological processes—which in the real world cannot be observed—can be simulated, visualized, and experienced in a sensory immersive environment. Thus a virtual environment permits learning in contexts that are difficult or impossible to experience in real life. Illustratively, a virtual environment can permit travel through the body's circulatory system, or motion among molecules. Similarly, a virtual environment can deliver a wide range of observational perspectives (from extreme close-up to great distance) which sometimes cannot be easily achieved in the real world. For example, a virtual environment can display a syringe needle penetrating a portion of an anatomy from a perspective of being inside the anatomy.

Virtual environments can also provide access to contexts that are dangerous (e.g., procedures that present an unacceptable risk to a patient) or cost-prohibitive in which to train. A virtual environment has the potential to increase trainee motivation by offering direct skill and knowledge development. Because it is computer-based, a virtual environment can be adaptable to its users, making accommodations or adjustments for the physical characteristics and preferences of a particular user. A virtual environment is also well suited for evaluation and certification of trainees' skill and knowledge mastery, since the training sessions can be easily monitored and recorded for review and assessment.

Virtual environments can also provide various advantages for social aid and developmental training for individuals with social impairment. For example, virtual environment may provide information to users experiencing deficiencies in social communication and interaction. Particular users who may benefit from this technology involve those diagnosed with autism spectrum disorder and experience deficiencies in verbal and non-verbal communication skills. The virtual environment may provide advanced techniques for the recognition of social cues present in non-verbal communication and body language and provide the information to the user in a manner understandable to the user. Because of the range in the severity of social deficiencies, a virtual environment may be adaptable to its users, making accommodations or adjustments for the preferences of a particular user. A virtual environment is also well suited for evaluation and certification of a user's social capabilities and may function as a training tool to easily monitor and record the user's training progress.

In some embodiments, an injection aid system can include a computing system having at least one processor and a memory device, the computing system configured to generate a virtual environment including a treatment target; a display device, coupled to the computing system, the display device configured to visually display the virtual environment; and an injection tool having a needle and a plunger. The computing system can be further configured to develop a recommended injection schedule. The recommended injection schedule can comprise injection information. The computing system can be further configured to generate a comprehensive mapping of the treatment target based a pre-operative imaging data of the treatment target and a scanned position of the treatment target. The pre-operative imaging data can comprise information representative of at least one of an underline musculature of the treatment target and a facial expression scan of the treatment target. The computing device can be further configured to generate a graphical representation of the virtual environment, wherein the graphical representation of the virtual environment is stereoscopic.

The treatment target can comprise live tissue. The treatment target can comprise an anatomic training model configured to receive at least a portion of the injection tool. The anatomic training model can be configured to provide feedback in response to interaction by the injection tool.

The display device can comprise a stereoscopic display configured to present a stereoscopic graphical representation of the virtual environment. The display device can be further configured to be mounted on a head of a user. The display device can be further configured to sense motion of the user's head and to transmit information representative of the sensed motion to the computing system. The display device can be further configured to project injection information, wherein the injection information is superimposed on a field of view of a user. The injection information can comprise at least one of a position of the injection tool, an angle of the injection tool, an injection location, an injection depth, an injection angle, an injection volume, a position of the treatment target, a medication type, a recommended injection schedule, and a comparison of a detected injection to the recommended injection schedule. The injected information can overlay the treatment target. The injected information is offset from a line of sight of the user. The injected information can be in the form of at least one of words, symbols, pictures, and video. The display device can comprise a remote screen display.

The injection tool can further comprise a positional sensor configured to sense a position and an orientation of the injection tool. The positional sensor can be configured to transmit information representative of the sensed position and orientation of the injection tool to the computing system. The injection tool can further comprise a force sensor configured to measure a force exerted on the plunger. The force sensor can be configured to and transmit information representative of the measured force exerted on the plunger to the computing system. The injection tool can further comprise a syringe or a catheter.

The injection aid system can further comprise an optical tracking system having a field of view. The optical tracking system can be configured to determine a three-dimensional position of at least one of the display device, the injection tool, and the treatment target. The optical tracking system can be configured to measure a displacement of the plunger. The optical tracking system can be positioned such that the treatment target is in the field of view of the optical tracking system. The injection tool can further comprise an alignment marker configured to reflect electromagnetic waves. The treatment target can further comprise an alignment marker configured to reflect electromagnetic waves. The optical tracking system can further comprise a light sensor; an infrared light source, positioned around the light sensor, configured to emit infrared light; an infrared filter positioned in front of the light sensor configured to cause the light sensor to detect infrared light emitted from the infrared light source; and a processor configured to periodically pulse on and off the infrared light source, the processor also configured to process infrared light, reflected from at least one of the injection tool and the treatment target and sensed by the light sensor, to determine a three-dimensional position of at least one of the injection tool and the treatment target.

The injection aid system can further comprise a scanner configured to measure a facial expression of the treatment target and determine an underlying anatomy and a muscle motion. The scanner can be further configured to interact with one or more landmarks on the treatment target to measure a location of at least one of the injection tool and the display device relative to the treatment target. The landmarks can comprise at least one of the center of an eyeball and an apex of a nose. The scanner can be further configured to detect a position of at least one of the display device, the injection tool, and the treatment target relative to a user.

The injection aid system can further comprise a glove configured to sense a position and an orientation a user's hand. The glove can be further configured to transmit information representative of the sensed position and orientation of the user's hand to the computing system.

In some embodiments, a method for providing a recommended injection schedule when using an injection aid system, the injection aid system including a display device and an injection tool, the method can include scanning a treatment target to obtain a scanned position of the treatment target relative to the display device; generating a comprehensive mapping of the treatment target; developing the recommended injection schedule, the recommended injection schedule comprising injection information; and projecting the injection information on the display device. The method can further comprise acquiring a pre-operative imaging data of the treatment target. The pre-operative imaging data can comprise information representative of at least one of an underline musculature of the treatment target and a facial expression scan of the treatment target. Generating a comprehensive mapping of the treatment target can comprise merging the pre-operative imaging data of the treatment target with the scanned position of the treatment target. The injection information can comprise at least one of a position of the injection tool, an angle of the injection tool, an injection location, an injection depth, an injection angle, an injection volume, a position of the treatment target, a medication type, and a comparison of a detected injection to the recommended injection schedule. Projecting the injection information on the display device can comprise superimposing the injection information on a field of view of a user. The injection information can overlay the treatment target. The injection information can offset from a line of sight of the user. The method can further comprise scanning a detected injection procedure. Scanning a detected injection procedure can comprise tracking at least one of a position and orientation of the injection tool and a displacement of a plunger of the injection tool. The method can further comprise comparing the detected injection procedure to the recommended injection schedule. The method can further comprise adjusting the recommended injection schedule according to the detected injection procedure. The method can further comprise receiving feedback information from the treatment target in response to an interaction between the injection tool and the treatment target. The method can further comprise determining a location of a hazard zone. The display device can comprise a stereoscopic display configured to present a stereoscopic graphical representation of the virtual environment. The display device can be further configured to be mounted on a head of a user.

In some embodiments, a method for injection training when using an injection aid system, the injection aid system including an injection tool and a treatment target, the method can include determining if a tip of the injection tool is located within a target location in the treatment target; detecting a force applied to a plunger of the injection tool; and calculating an accumulated injection amount based on the detected force applied to the plunger. The method can further comprise comparing the calculated accumulated injection amount to a target injection amount. The method can further comprise distorting a model mesh relative to the accumulated injection amount. Distorting a model mesh can comprise moving at least one vertices of the model mesh away from a location of the tip of the injection tool proportional to the accumulated injection amount. The method can further comprise determining a training score. The method can further comprise reporting to a user the training score.

In some embodiments, a social aid system can include a computing system having at least one processor and a memory device, the computing system configured to process a social cue information and generate a virtual environment including an observed target; a display device, coupled to the computing system, the display device configured to visually display the virtual environment; and a scanner having a field of view. The computing system can be further configured to develop a recommended social response, wherein the recommended social response comprises the social cue information. The computing system can be further configured to generate a graphical representation of the virtual environment. The graphical representation of the virtual environment can be stereoscopic. The observed target can comprise a human. The computing system can be further configured to provide feedback in response to a social interaction by the observed target.

The display device can comprise a stereoscopic display configured to present a stereoscopic graphical representation of the virtual environment. The display device can be further configured to be mounted on a head of a user. The display device can be further configured to sense motion of the user's head and to transmit information representative of the sensed motion to the computing system. The display device can be further configured to project at least one of the social cue information and a recommended social response, wherein the injection information is superimposed on a field of view of a user. The social cue information can comprise at least one of a facial expression, a facial color, a facial motion, a body language, a voice tone, a speech pace, and a buried frequency. The social cue information can overlay the observed target. The social cue information can be offset from a line of sight of the user. The injected information is in the form of at least one of words, symbols, pictures, and video. The display device can comprise a visor lens and a project, wherein the projector configured to project at least one of the social cue information and the recommended social response onto the visor lens. The display device can comprise a positional sensor configured to sense a position and an orientation of the display device. The positional sensor can be configured to transmit information representative of the sensed position and orientation of the display device to the computing system.

The scanner can be configured to obtain information representative of at least one of the social cue information, a position of the observed target, an underlying anatomy of the observed target, and a muscle motion of the observed target. The scanner can be configured to determine a three-dimensional position of at least one of the display device, a user, and the observed target. The scanner can be configured to track one or more landmarks on the observed target to measure at least one of a movement of the observed target and a location of the observed target relative to a user. The landmarks can comprise at least one of the center of an eyeball and an apex of a nose. The scanner can comprise at least one of an eyeglass camera, a lapel camera, a mobile device camera, and a wearable device camera.

In some embodiments, a method for providing a recommended social response when using a social aid system, the social aid system including a display device, the method can include scanning an observed target to detect a social cue information relating to the observed target; generating a comprehensive map of the observed target; developing the recommended social response, the recommended social response comprising the social cue information; and projecting the recommended social response on the display device. The social cue information can comprise information representative of at least one of at least one of a facial expression, a facial color, a facial motion, a body language, a voice tone, a speech pace, and a buried frequency, a position of the observed target, an underlying anatomy of the observed target, and a muscle motion of the observed target. Generating a comprehensive map of the observed target can comprise analyzing the social cue information to generate an emotional state of the observed target. Projecting the recommended social response on the display device can comprise superimposing at least one of the social cue information and the recommended social response on a field of view of a user. The projected recommended social response can overlay the observed target. The projected recommended social response can be offset from a line of sight of the user. The method can further comprise scanning a detected social response of a user. Scanning a detected social response can comprise tracking a position and orientation of the user. Scanning a detected social response can comprise capturing at least one of an audio recording and video recording of the detected social response. The method can further comprise comparing the detected social response to the recommended social response. The method can further comprise adjusting the recommended social response according to the detected social response. The method can further comprise detecting feedback information from the observed target in response to the detected social response. The display device can comprise a stereoscopic display configured to present a stereoscopic graphical representation of the virtual environment. The display device can be further configured to be mounted on a head of a user.

Any feature, structure, or step disclosed herein can be replaced with or combined with any other feature, structure, or step disclosed herein, or omitted. Further, for purposes of summarizing the disclosure, certain aspects, advantages, and features of the inventions have been disclosed herein. It is to be understood that not necessarily any or all such advantages are achieved in accordance with any particular embodiment of the inventions disclosed herein. No individual aspects of this disclosure are essential or indispensable.

DETAILED DESCRIPTION

Aspects of the disclosure are provided with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit scope of the disclosure herein, which is instead defined by the claims following this description.

Disclosed herein are systems, devices and methods for virtual reality and/or augmented reality for aid and training in the medical and social arts.

Injection Aid System Utilizing Virtual Reality

The disclosed systems and methods can be applied to the aid, training, evaluation, and certification of health-care professionals performing a variety of medical injection procedures including prophylactic, curative, therapeutic, acupuncture, or cosmetic treatments. Illustratively, the user can virtually access a portion of the anatomy of interest, such as, for example, the face. Employing various types of user interface devices such as, for example, an injection tool configured to operate as a syringe, the user can deliver one or more injections to a portion of anatomy of interest and/or simulate the process of delivering one or more injections.

Figure 1:
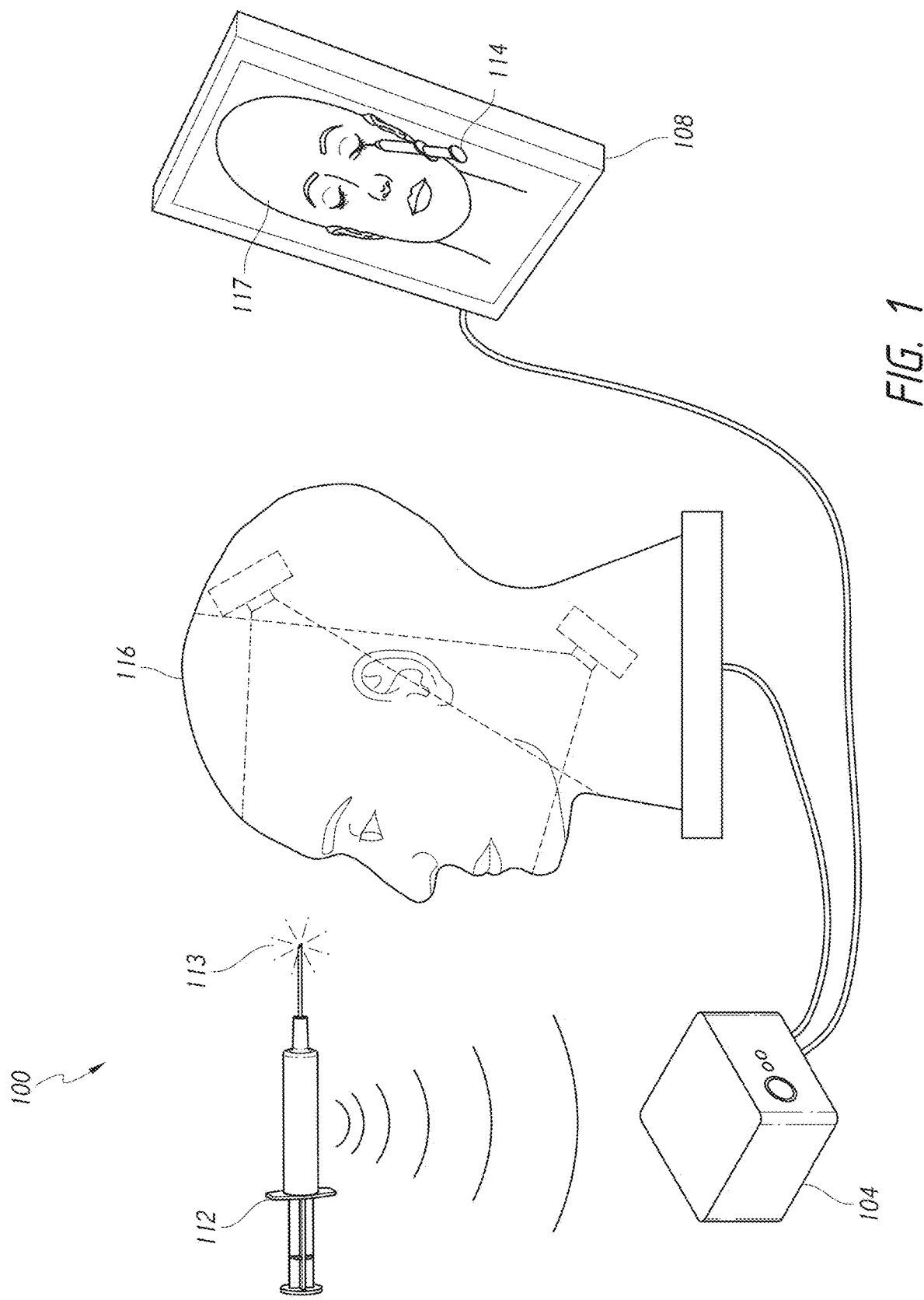
FIG. 1 illustrates an injection aid system according to one embodiment herein.

FIG. 1 illustrates an injection aid system 100 configured to generate a virtual environment in which a user may be engaged. In one embodiment, the injection aid system 100 comprises several components: (1) a computing system 104 configured to generate a virtual environment; (2) a display device 108 configured to present visual images of the virtual environment; (3) an injection tool 112 having a needle configured to enable simulation and/or actual injection by the user; and (4) a treatment target 116 that may comprise live and/or artificial tissue. The display device 108 may be coupled to the computing system 104 and configured to present visual images depicting the virtual environment generated by the injection aid system 100. The injection aid system 100 may use information available to a user to provide the user with more complete and accessible information. The information may advantageously result in more informed treatment procedures and superior outcomes.

The injection aid system may include a treatment target 116. In the illustrated example, the treatment target 116 is in the form of an artificial head, but the treatment target 116 can include any target (live or artificial) appropriate for a medical injection procedure.

The treatment target 116 can provide tactile feedback by applying force (actively or passively) in response to the injection motions or other physical interaction of the user. Illustratively, the treatment target 116 can be configured to emulate structural characteristics of the portion of the anatomy of interest. For example, one embodiment of a treatment target 116 features an anatomically accurate model of a human or human body part (such as a face) to be used for injection training. In an embodiment, the anatomical model can include various injection conditions, such as, for example, layered skin, available in multiple tones and textures to mimic a diverse span of age, race, and skin texture. In an embodiment, the layered skin can be removable and/or replaceable. The anatomical model can include additional simulated injection conditions such as, for example, muscle tissue, nerve tissue and skeletal tissue. In an embodiment, the treatment target 116 can simulate any human or animal part, such as, for example, the face, head, brain, neck, back, chest, spine, torso, arms, legs, hands, feet, mouth, or any other body part or portion of the body of interest. In some embodiments the treatment target 116 need not be an accurate representation of a specific portion of anatomy because the virtual environment can visually superimpose anatomical structure in the treatment target 116 within the virtual training environment. Accordingly, the treatment target 116, having certain physical characteristics of an anatomy, can be used to support training of procedures directed at multiple portions of anatomy. In some embodiments, the treatment target 116 can be configured to mimic certain muscle contraction conditions common with a particular type of injection. For example, this can include contractions of facial features, such as furrowing of an eyebrow, squinting of the eyes, or pursing of the lips. The removable skin can also include blemishes, such as scars or wrinkles. The treatment target 116 may include one or more optical trackers inside the treatment target 116 capable of detecting a light point.

The treatment target 116 may include living tissue in the case of a treatment procedure being performed on a live patient.

FIG. 1 illustrates the injection aid system 100 including an injection tool 112. In some embodiments, the injection tool 112 is configured to sense its position and orientation in space, and to transmit its position and orientation information to the computing system 104. The computing system 104 incorporates the position and orientation information into the virtual environment displayed to the user. The injection tool 112 may include one or more sensors to measure the position and orientation in three-dimensional space of the injection tool 112. The sensors may communicate the position and orientation information to the computing system 104, such that the injection tool 112 can be displayed in the virtual environment. In the illustrated example, the injection tool 112 is in the form of a syringe, but the injection tool 112 can include other needle-based devices or catheter devices.

In some embodiments, the injection tool 112 comprises a track needle tip and is configured to simulate a syringe, including a plunger. The injection tool 112 may also include one or more sensors configured to measure the amount of force applied by the user on the plunger of the injection tool 112 during an injection. The measured force can be communicated to the computing system 104 such that motion of the plunger and the actual and/or simulated injection of material can be displayed in the virtual environment. In some instances, the injection tool 112 is configured to measure the displacement of the plunger as the injection is being performed. The displacement information is transmitted to the computing system 104 and displayed within the virtual environment.

In some embodiments, the treatment target 116 is configured to sense physical interaction with objects, such as, for example, the injection tool 112 or the user's hand. Information corresponding to the sensed physical interaction is transmitted to the computing system 104 and incorporated into the virtual environment. Physical interaction between the user, the injection tool 112, and the treatment target 116 may be captured by an external sensing system, such as, by way of non-limiting example, an optical tracking system. The optical tracking system can be configured to obtain position, orientation and motion information of the user, the injection tool 112, the treatment target 116, and other objects used in the injection aid system 100. The information sensed by the optical tracking system can be transmitted to the computing system 104. The computing system 104 is configured to receive the information and to display it in the virtual environment in a realistic manner. Optical tracking systems offer some advantages over other approaches to measure and determine the position and orientation of an object in three-dimensional space. For example, optical tracking is less susceptible to noise from the environment, such as, for instance, ferromagnetic metal in the environment which can influence the accuracy of the measurements of magnetic tracking systems. Additionally, optical tracking does not suffer from drift problems experienced in, for instance, inertial sensors, which cause measurements to slowly deviate from actual values, for which compensation techniques must be applied. Optical tracking also allows for many objects to be tracked simultaneously. Optically tracked devices can be lightweight and they do not require wires or power. As such, users are neither hampered by wires nor limited in their manipulation of the object.

In some embodiments, a sensor, such as, for example a camera, is placed within or proximate to the treatment target 116 to gain a perspective of the injection tool 112 from a perspective interior to the treatment target 116 during an injection. The sensor can detect and transmit information to the computing system 104 which can display the results in the virtual environment.

The optical tracking system may detect the position and orientation of the injection tool 112 in three-dimensional, physical space. The optical tracking system can also be configured to measure the displacement of the plunger, in three-dimensional, physical space, to estimate the rate at which a therapeutic agent would be delivered in the actual and/or simulated injection. The optical tracking system may include an integrated network system in the injection tool 112 capable of communicating with the computing system 104.

Figure 4:
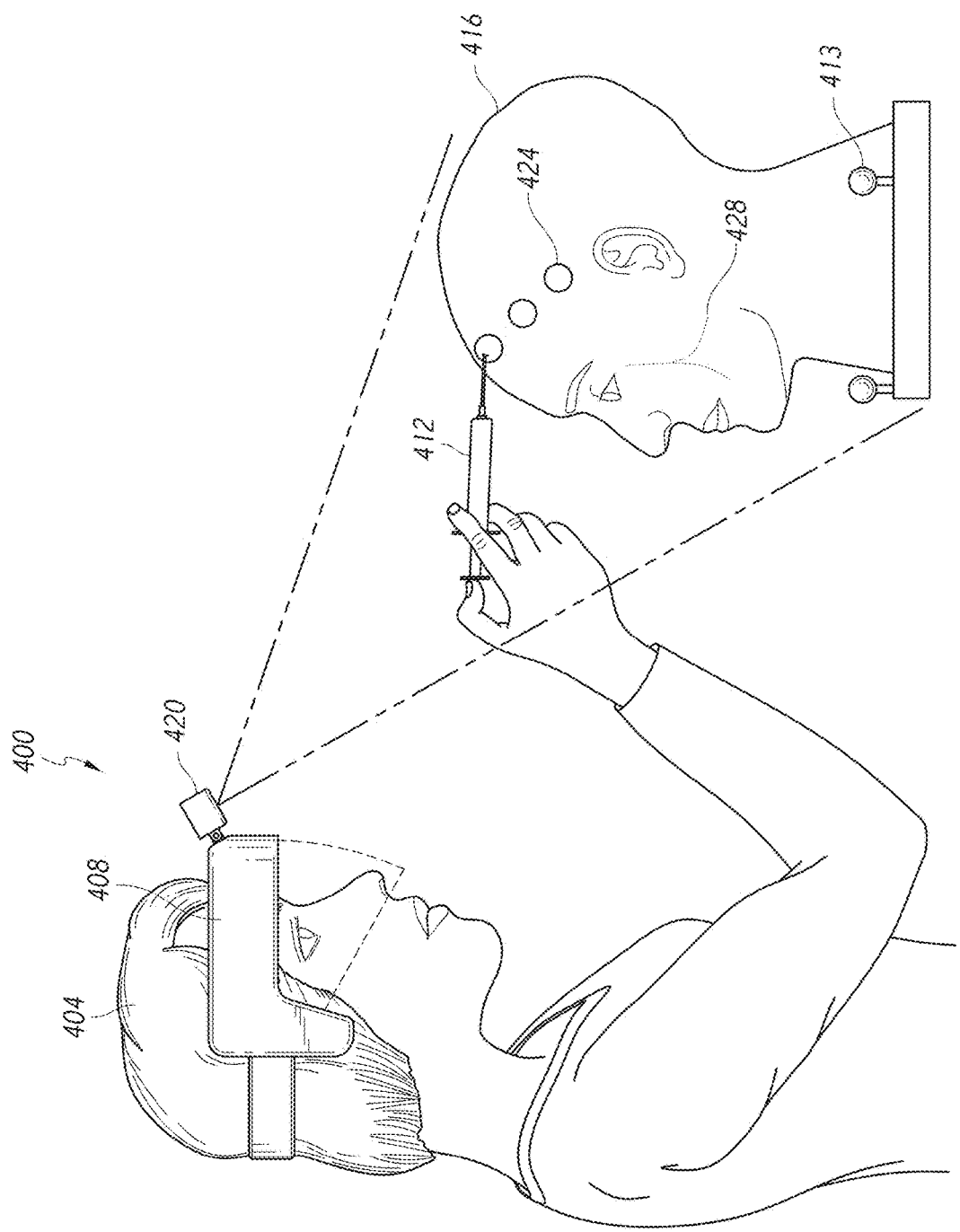
FIG. 4 illustrates another embodiment of the injection aid system according to one embodiment herein.

In some implementations, the optical tracking system periodically emits a light or other source of electromagnetic radiation which is reflected from the injection tool 112 and/or the treatment target 116 back to the optical tracking system. In some embodiments, the optical tracking system senses light from the injection tool 112 and/or treatment target 116 directly. The optical tracking system may sense light emitting from an alignment target 113 at the head of the injection tool 112 and/or sense light emitting from an alignment target 413 at the base of the treatment target 416 (as shown in FIG. 4). The alignment target 113, 413 may comprise a light source. For example, the light source may use a fiber optic. The light source may be one or more LEDs, laser diodes, or any other light emitting device or combination of devices. The injection aid system 100 may include a digital model of the treatment target 116 with anatomical information and software able to combine the injection tool 112 and/or needle tip position 113 in the treatment target 116 with the digital model.

As illustrated in FIG. 1, the display device 108 comprises a remote screen display configured to provide images of the generated virtual environment. The injection aid system may provide information and training results of injections to a user through, for example, a patient's face shown on the display device 108, such as on a tablet, mobile device, laptop or standalone display. The display device 108 may include wearable glasses or as otherwise described herein. The display device 108 can be used to overlay a computer-generated three-dimensional image(s) on the treatment target 116. The computer-generated image(s) can correspond to one or more layers of anatomy (e.g. bones, nerves, blood vessels, or the like) for the specific target. The images can be obtained using a CT scan, an MRI scan, a photographic image, an X-ray, and/or the like.

The computer-generated image(s) may be used in conjunction with the medical injection treatment so that the locations of structures in the image correspond to the actual location of those structures in the treatment target 116. The ability to visualize the tissue layers as the user is performing a procedure can help the user perform the procedure at an optimal location. For example, the user can be instructed by the injection aid system 100 via the display device 108 to guide the injection tool 112 to an appropriate depth for a therapeutic injection. The movement of the injection tool 112 can be projected on the display device 108 in real-time during the treatment procedure. Thus, as the injection tool 112 is moved through the treatment target 116, the location of a distal tip of the injection tool 112 can be viewed on the computer-generated image. When the distal tip of the injection tool 112 is positioned in the target location in the treatment target 116, the distal tip of the injection tool 112 is positioned in the target location in the image.

The generated virtual environment can depict a portion of an anatomy into which the injection can be delivered. Display of the anatomy is not limited to constraints found in the physical world. Accordingly, the user can select a display format that provides increased or altered perception of the virtual anatomical structure being injected. Illustratively, the user may desire to see the underlying structure of the anatomy, such as bones, nerves, blood vessels, or the like. By implementing a virtual environmental control, such as for example, a hand gesture, the user can cause to be displayed the desired portion of the anatomy. In a similar manner, the user can change perspective views of the virtual anatomy by, for example, zooming in or out, panning left or right, or rotating up, down or around the virtual anatomy.

The user can simulate an injection by moving the injection tool 112 in the physical world and having such motion depicted in the virtual world, as described above. Illustratively, the injection tool 112 is depicted as a syringe approaching an identified target on the treatment target 116. In some embodiments, a target image (for example, a bull's eye display) is superimposed on the virtual anatomy 117 for the user to more easily identify the desired injection location. The injection aid system 100 is able to display a virtual tool 114 relative to the virtual anatomy 117 based on communicated positions and orientation information provided by the injection tool 112. In the virtual environment, as the injection tool 112 approaches the treatment target 116, sensory indicators may be displayed, in an overlay manner for example, to indicate proximity of the virtual tool 114 to the desired target location. Such sensory indicators may include, by way of non-limiting example, audible sounds or visual displays. As the virtual tool 114 approaches and penetrates the virtual anatomy 117, the user can apply pressure to the plunger of the injection tool 112. The pressure information is communicated to the computing system 104 which generates an image of the virtual tool 114 being injected in the virtual environment. In some implementations, the virtual environment can display the therapeutic agent being delivered to the virtual anatomy 117. In certain perspectives of the virtual anatomy 117 below the skin, images of the therapeutic agent exiting the virtual tool 114 and flowing into the virtual anatomy 117 may be provided.

Figure 2A:
FIG. 2A is a front perspective view of another embodiment of the injection aid system.
Figure 2B:
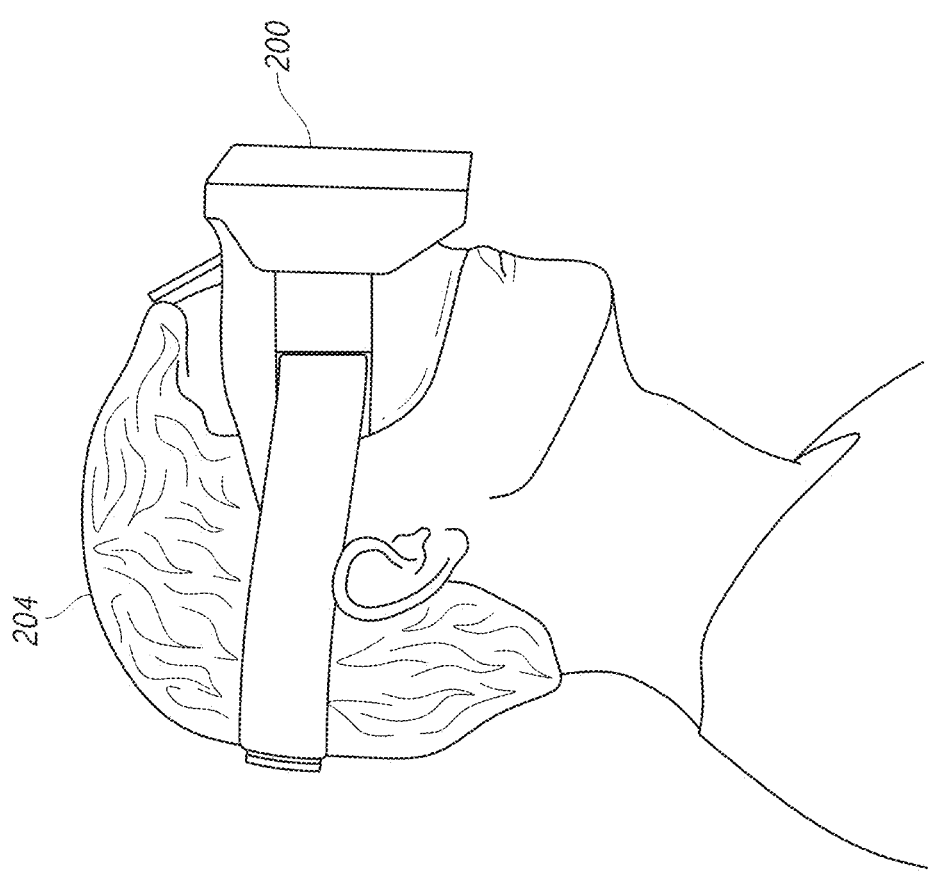
FIG. 2B is side perspective view of the injection aid system of FIG. 2A.

FIGS. 2A and 2B illustrate another embodiment in which the display device 200 comprises a head-mounted display to be worn by a user 204. The display device 200 is configured to provide stereoscopic images of the generated virtual environment. The computing system 104 is configured to simulate an environment with a sufficient degree of fidelity to cause the user to perceive that he or she is present and engaged in a realistic scenario. In an embodiment, the computing system 104 generates stereoscopic images (also referred to as three-dimensional images) of the environment to create the illusion of depth by presenting two separate, offset images to the user's left eye and right eye. The separate, two-dimensional images are combined in the user's brain to create a perception of three-dimensional depth and texture. As illustrated in FIGS. 2A and 2B, use of a stereoscopic, head-mounted display device 200, such as, by way of non-limiting example, the Oculus Rift, offered by Oculus VR of Menlo Park, Calif., can help to realize such a perception for the user 204. The stereoscopic, head-mounted display 200 can provide a wide field of view, stretching beyond the user's peripheral vision. In some embodiments, the head-mounted display 200 includes the capability to track motions of the user's head, which are transmitted to the computing system 104. The computing system 104 modifies the orientation of the virtual environment in response to the user's head motion, thereby creating for the user 204 a sense of presence within the virtual environment. The combination of the wide field of view with the features of head-tracking and stereoscopic, three-dimensional imaging can create a natural, intuitive, and immersive experience for the user.

Figure 3:
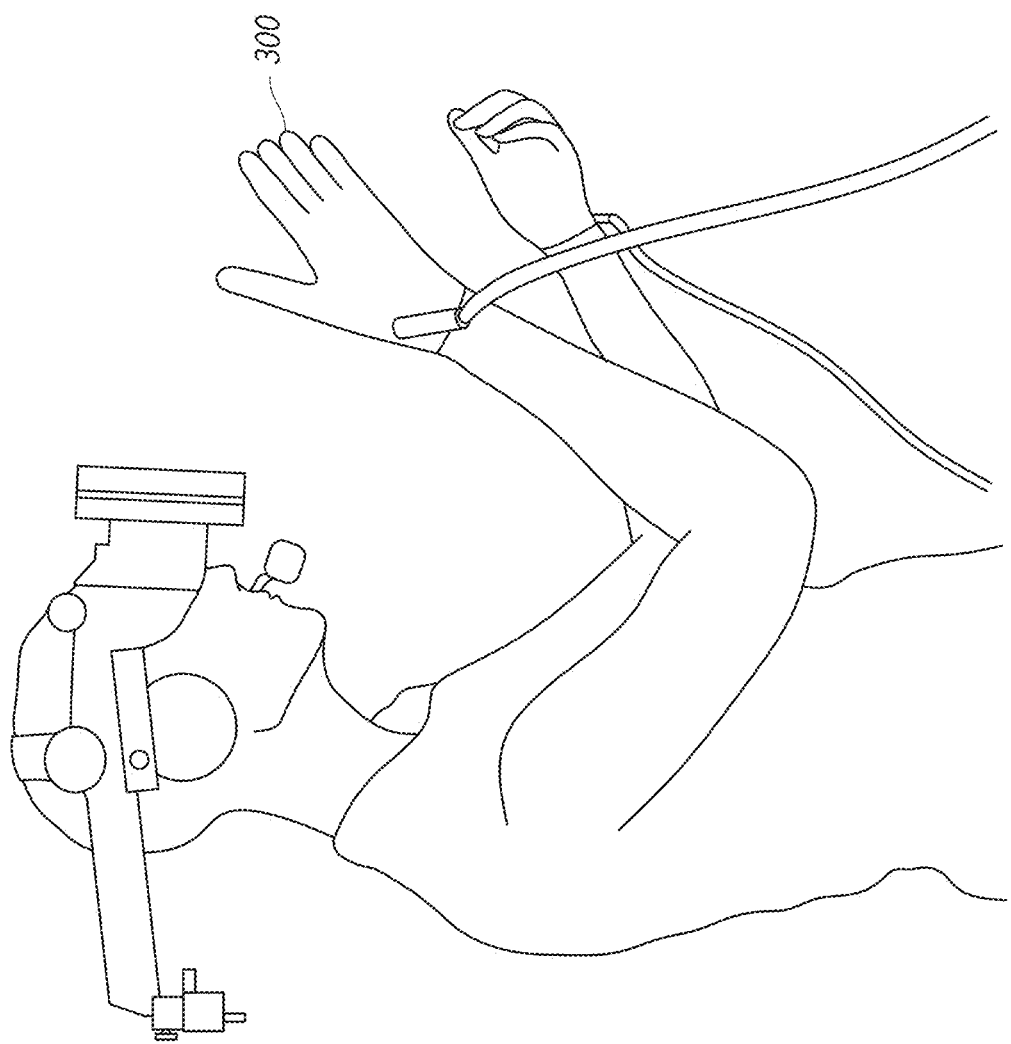
FIG. 3 is a side perspective view of another embodiment of the injection aid system disclosed herein.

In an embodiment, the injection aid system 100 can include one or more sensor-equipped, gesture control gloves 300, as illustrated in FIG. 3. The control gloves 300 may be configured to sense the position, orientation and motion of the user's hand or hands as the user 304 interacts with at least one of the virtual environment, the injection tool 112, and the treatment target 116. The injection aid system 100 may include an optical tracking system configured to sense and measure position, orientation, and motion of the control gloves 300. The computing system 104 may be configured to incorporate the glove's position and orientation information into the virtual environment displayed to the user. Advantageously, the computing system 104 may process position, orientation, and motion information corresponding to multiple objects (such as the testing tool, the injection apparatus, the user's hand, the user's head and body, etc.) in such a manner so as to realistically display the interaction of the objects in the virtual environment.

According to some embodiments, the disclosed systems and methods can enable users to train for and practice a variety of injections, ranging from on-label to off-label product injections. In some embodiments, the system may allow users to train for therapeutic treatments. In other embodiments, the system may allow users to train for injections into arteries, bone marrow, the spine, the sternum, the pleural space of the chest region, the peritoneal cavity, joint spaces, internal organs, or any other injection sites. The injection aid system 100 may be used for any type of injection, including, but not limited to those involving prophylactic, curative, therapeutic, acupuncture, or cosmetic treatments in humans and in animals. In other applications, the systems and methods disclosed herein can be used for dental application and for training of dental procedures.

A personalized 3D facial model, developed as described above, can also be used for visualizing the result of plastic surgery procedures. For example, using simulated injections performed by a training tool, in an augmented reality mode for filler injection modeling and visualization, the area of the face could expand relative to the amount of product simulated to have been injected.

Some of the features included in viewing anatomy in virtual reality for aid in providing treatment and training include allowing the user to see a virtual reality face from different angles. The user can remove layers of anatomy to reveal underlying tissues and structures of the anatomy. Three-dimensional interactive exploration of injection sites can be performed to identify nearby nerves and vessels. The user can be asked examination questions and be required to identify specific objects or locations within the anatomical model.

In some implementations of the above-described embodiments, an augmented or virtual reality display (e.g., wearable glasses or as otherwise described above) can be used to overlay a computer-generated image on a training apparatus. The training apparatus can be model of any anatomical part of a human or animal. For example, the training apparatus can be modeled after a human head. For more information on the training apparatus or model, see U.S. Publication No. 2014/0212864, filed Mar. 31, 2014, titled "INJECTION TRAINING APPARATUS USING 3D POSITION SENSOR," which is included in the Appendix. The computer-generated image can correspond the facial features (or other anatomical feature) of an actual patient (e.g., the skin tone, skin type, or facial features) or any layer of anatomy (e.g., bones, nerves, blood vessels, or the like). As described above, the images can be obtained using a CT scan, an MRI scan, a photographic image, an X-ray, or the like. The ability to mimic the actual patient can help the clinician or patient visualize the potential impact of a procedure on the patient's actual face.

The user can simulate a procedure by operating a testing tool in connection with the training apparatus (e.g., a syringe or other needle based device). Features of the testing tool can be found in U.S. Publication No. 2014/0212864, filed Mar. 31, 2014, titled "INJECTION TRAINING APPARATUS USING 3D POSITION SENSOR," which is incorporated herein by reference. The movement and potential impact of the testing tool can be seen through the computer generated image of the display device. For example, if the testing tool is a syringe being used to mimic the injection of a substance into a patient's face, the likely impact on the patient's face can be visualized through the display device as the plunger of the syringe is depressed. As another example, if the testing tool is a suction device being used to remove a substance from the patient's face, the likely impact on the patient's face can be visualized through the display device as the actuator is retracted or otherwise activated. In any of these scenarios, the display device can overlay images of the patient's anatomy on the training apparatus to mimic the changes in the anatomy during the use of the testing tool. The displayed images can be real-time and/or progressive over the duration of the procedure. These features can help a clinician or patient understand the likely impact of a procedure and/or how a product performs. In some configurations, an image of the anatomy modified by the procedure can be displayed on a portion of the training apparatus, while the original anatomy can be displayed on another portion of the training apparatus, so the clinician or patient can easily visualize the differences.

Augmented Reality System for Injection Aid

Figure 5:
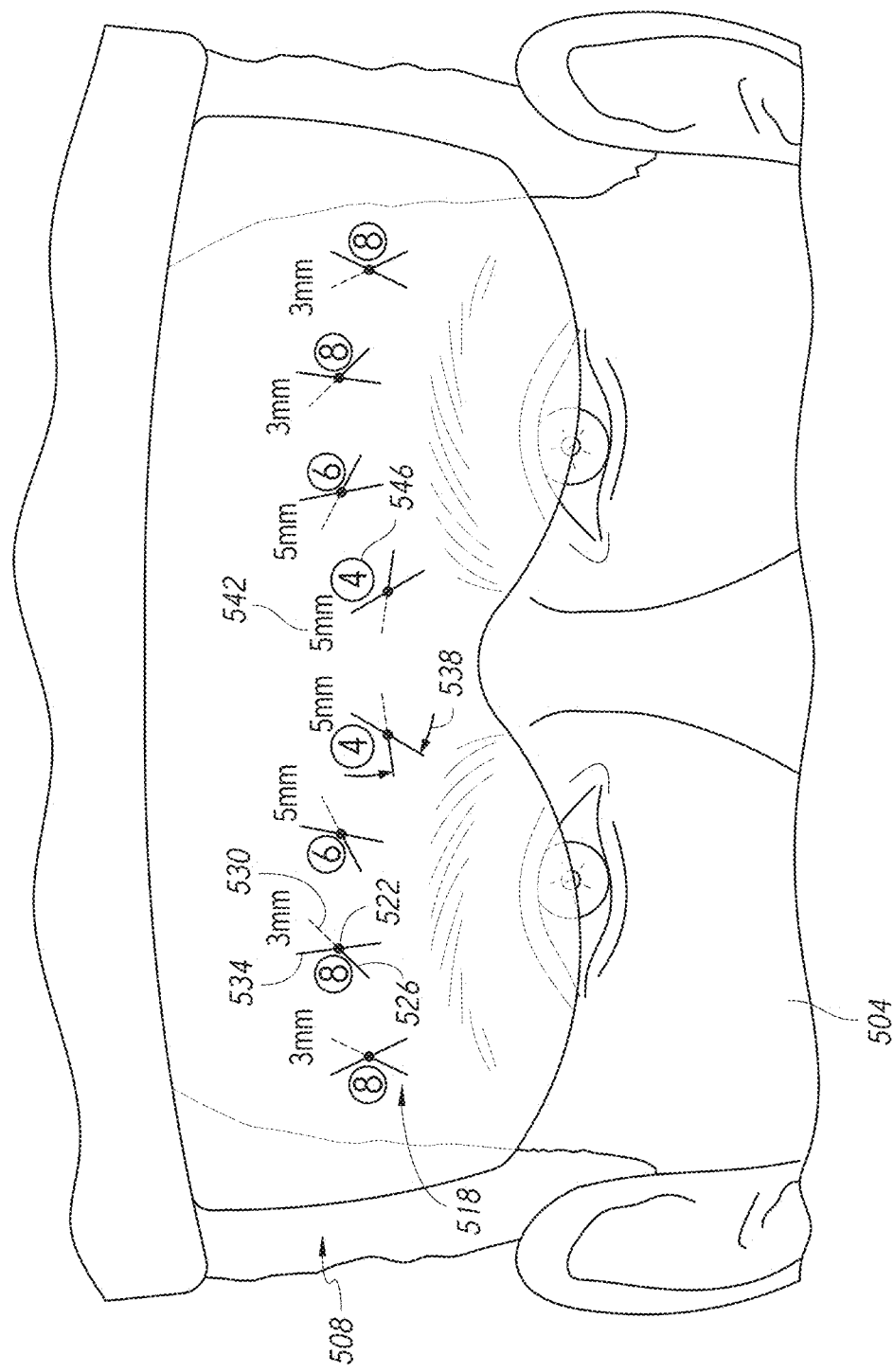
FIG. 5 is a front view of a display device of the injection aid system of FIG. 4.

FIGS. 4 and 5 show another embodiment of the injection aid system 400. The injection aid system 400 resembles or is identical to the injection aid system 100 except as described differently below. Accordingly, numerals used to identify features of the injection aid system 400 shown in FIGS. 4 and 5 identify like features of the injection aid system 100 shown in FIGS. 1-3. The foregoing descriptions can be combined with the specific discussion below in other various embodiments.

As discussed herein, the virtual representation of the patient's anatomy may be used as an aid during the actual injection procedure and/or during educational training sessions. Augmented reality displays may be employed in the injection aid system, discussed above. By way of non-limiting examples, augmented reality displays may include wearable glasses permitting the user to see the physical world, while also providing computer-generated images to be overlaid on the user's field of view. Accordingly, a model based on the patient's anatomy can be generated by the injection aid system 400. Information specific to the patient's anatomy can be displayed to the user 404 by way of the augmented reality display. For example, a graphical overlay, identifying the target 424 location for injection and the vital structures 428 to be avoided can be superimposed on the user's field of view during the procedure (or during training for the procedure) to assist in delivering the injection to the desired location.

FIG. 4 illustrates an injection aid system 400 comprising several components: a display device 408 configured to present visual images superimposed on the user's field of view; an injection tool 412 having a needle configured to enable simulation and/or actual injection by the user 404; and a treatment target 416 that may comprise live and/or artificial tissue. The injection aid system 400 may include a computing system configured to generate the augmented environment. The display device 408 may be coupled to the computing system and configured to present visual images depicting the augmented environment generated by the injection aid system 400. The injection aid system 400 may use information available to a user 404 to provide the user 404 with more complete and accessible information. The information may advantageously result in more informed treatment procedures and superior outcomes.

The injection aid system 400 may utilize a display device 408 incorporating augmented reality to display information into the user's field of view. Augmented reality glasses can be used to enable a user 404 to see an outline of a treatment target 416 with a projection of the patient's face superimposed on the treatment target 416. The user 404 can interact with and receive feedback from the treatment target 416. In some instances, the injection aid system 400 may provide the user 404 with changes to at least part of the anatomy (e.g., the patient's face) projected on the display device 408 through the use of augmented reality.

In some embodiments, the display device 408 includes an augmented reality glasses, holographic projection, or other augmented reality tools to display a model of the patient's anatomy. The display device 408 may comprise a stereoscopic, head-mounted display device, such as, by way of non-limiting example, the Oculus Rift, offered by Oculus VR of Menlo Park, Calif. and the HoloLens, offered by Microsoft. The display device 408 may consist of a headband with a see-through visor. The display device 408 utilizing augmented reality may be used in conjunction with or as a replacement to a screen display device, as discussed above.

The display device 408 may comprise a stereoscopic display upon which information can be projected that appears to be realistic or symbolic. The information may appear positioned in space ahead of the user 404 of the display device 408. For example, the information may appear projected onto the display device 408, floating adjacent to a physical surface, and/or floating in space. The projected information can be in the form of numerical values, colored shapes, bar charts, grids, tissue structures including arteries veins, fat, muscles and nerves, as discussed in further detail below. In some instances, the display device 408 allows the user 404 to interact with the display device 408. The injection aid system 400 may communicate with the injection tool 412, as the injection tool 412 interacts with a treatment target 416 (artificial or living), to provide more complete and accessible information to the user 404.

In some embodiments, the injection aid system 400 includes a scanner 420. The scanner 420 may provide see through experience to the user 404 and can be mounted on the display device 408. The scanner 420 is configured to track facial expressions, collect multiple high-resolution scans, and determine underlying anatomy, and muscle motion. The injection aid system 400 may utilize the information acquired by the scanner 420 to generate anatomical models, as described in further detail below. The scanner 420 may detect relative position of at least one of the display device 408, the injection tool 412, and the treatment target 416, as shown in FIG. 4. The scanner 420 allows the injection aid system 400 to detect the position of the treatment target 416. As illustrated in FIG. 4, the treatment target 416 may comprise an artificial head. In some embodiments, the treatment target 416 may comprise an anatomical feature of a human patient. With the treatment target 416 position known, the user 404 may view the treatment target 416 through the display device 408 while appropriate information appears to be projected on the treatment target 416.

FIG. 5 illustrates a display device 508 that may selectively display information to the user 404. By way of non-limiting example, the information projected on the display device 508 may include position and angle of the injection tool 412, track of needle tip, location of injection, injection track, depth of injection, angle of injection, volume of injection, position of targeted anatomy, optimum position and track, comparison to optimum technique as well as testing and scoring information. This information may be projected to appear in the field of view of the user 404 and avoid the need to shift attention from treatment target 416 to a remote display screen.

The information displayed on the display device 408 may include information acquired by a scanner 420. The information may include anatomical models generated by the injection aid system 400, as described herein. The injection aid system 400 may project the information on the display device 408 in a method that is readily understandable to the user 404. In some instances, the injection aid system 400 converts the acquired and/or generated information into a code or pictorial representation. The injection aid system 400 allows the user 404 to review the procedure information, while not having to look away from the treatment target 416.

FIG. 5 illustrates one such embodiment of information that can be seen on the display device 508. As discussed above, the information can include, preferred injection sites, with color and or shape symbols coded to indicate medication type, volume depth of injection along with needle angle, medication delivery guides and nearby anatomy risks. The anatomy in the digital model may be projected to appear on the treatment target 416. The injection aid system 400 may simulate the under skin anatomical features as a see through view able to convey critical tissue information such as arteries, veins, nerves, fat and muscles as the injection tool 412 is projected on the image of the treatment target 416. In the illustrated embodiment, the display device 408 may project one or more treatment icons 518. Each treatment icon 518 may represent an injection site on the treatment target 416. The penetration point may be represented by a penetration indicator 522. The injection track may be represented by track icon 526. The injection aid system 400 may provide information relating to the angle formed between the injection tool 412 and the treatment target 416 during treatment by the treatment angle icon 538. The treatment angle icon 538 may be formed between a skin track icon 526 and angle track 534. The skin track icon 526 may represent an orthogonal projection from the surface of the treatment target 416 at the injection site. The track icon 526 may correspond to a depth icon 530 representing an injection depth. The injection aid system 400 may represent the injection depth by a numerical depth icon 542. The treatment icon 518 may contain information including a volume medication to be injected, as represented by the volume indicator 546.

The information projected on the display device 408, 508 can be aligned with the treatment target 416, such as an artificial head or a patient's face, using one or more alignment target(s) 413. In this manner, a treatment icon 518 may be positioned on the display device 408 so that the treatment icon 518 is aligned with an actual injection site on the treatment target 416. By way of non-limiting example, the alignment target(s) 413 can be anatomical features, such as the center of an eyeball or an apex of the nose. The alignment target(s) 413 may comprise markers, such as reflective beads, that can be positioned on the patient when an image of the patient is captured. This allows the markers to appear in the captured image(s). As shown in FIG. 4, a plurality of alignment targets 413 can be positioned around an outer periphery of the treatment target 416. The alignment target(s) 413 may remain on the treatment target 416 during the entirety of a treatment procedure. The alignment target(s) 413 may be placed during an initial image capture and be positioned again on the patient in the same location during the treatment procedure. During the treatment procedure, the user 404 can align the alignment target(s) 413 in the computer generated image with the markers on the patient's face. In some embodiments, the injection aid system 400 can include a camera that captures the location of the alignment target(s) 413 during the treatment procedure. The camera may automatically align the alignment target(s) 413 in a computer generated image with the alignment target(s) 413 on the treatment target 416.

In some instances, the injection aid system 400 incorporates a blended augmented reality system with data from an imaging modality to enable live tissue injections. A patient imaging data is converted to a digital format. Then an injection aid system 400 may determine the preferred injection schedule. The injection schedule may include information relating to the medication type, injection locations, angles, depth, volume, and additional information discussed herein. In some embodiments, the injection aid system 400 may determine the location of particular hazard zones. The hazard zone may be projected onto the display device 408, 508 to avoid misplaced medication and/or resulting harm. A user 404 wearing the display device 408 may look toward the treatment target 416 to allow the scanner 420 to map the treatment target 416. The injection aid system 400 merges the patient imaging data with the scanned position of the patient relative to the display device 408. The user 404 may maneuver as required to perform the medical injection procedure as guided by the information projected on the display device 408 that appears on the patient skin. The user 404 may interact with the real patient while concurrently viewing the treatment information. For example, a user 404 may use the display device 408 to identify the location of high risk tissue to avoid the accidental misplacement of medication and resulting health impact.

In some embodiments, the injection aid system 400 incorporates an injection assistance using a remote advisor. The injection aid system 400 utilizes a remote viewing device, such as full immersion virtual reality goggles or open displays. The remote viewing device permits a remote treatment expert to view the treatment procedure in real time. The remote treatment expert may communicate with the user 404 to assist in a medical injection procedure and/or a training procedure to transition to treating living patients.

While certain embodiments of the systems and methods disclosed herein are directed to injection training, the disclosed systems and methods are not limited to such applications. The disclosed systems, devices and methods can be directed at delivering training for the clinical practice areas of diagnosis, therapeutic treatment, and delivery of medical procedures, as well as for the subject areas of anatomy and physiology, among others. Illustratively, a user can engage the virtual environment through the use of peripheral devices such as a head-mounted, stereoscopic display, a game-style controller, a pair of sensor-equipped gloves, one or more custom input/output tools, etc. Equipped with such instruments to simulate an environment, the user navigates through the virtual anatomy, exploring it and manipulating it. The virtual anatomy responds interactively to the motions and actions of the trainee and the objects. In an embodiment, the system includes one or more structures configured to interact with the trainee to simulate the tactile experience of anatomical engagement.

Generation of the Anatomical Model

In some implementations, the anatomical model depicted in the virtual environment is based on a patient's specific physiology. The injection aid system 100, 400 may utilize various patient facial expressions scans to develop a comprehensive mapping of the patient's underline musculature and more accurately develop a targeted treatment plan. Definition of the patient's anatomy can be obtained by, for example, a CT scan, an Mill scan, a photographic image, an X-ray, or the like, and used to form the anatomical model depicted in the virtual environment. Images of the treatment target, such as a live patient or artificial tissue, may be acquired through use of a camera or scanner 420 of the injection aid system 100, 400. In such circumstances, clinicians can practice delivering injections to a representation of an anatomy corresponding to an actual patient.

Illustratively, one or more three-dimensional scans of a patient's face (or other portion of the patient's anatomy), can be performed by initially scanning the patient's face. The injection aid system 100, 400 may utilize a scanner 420, as discussed above, to track facial expressions, collect multiple high resolution scans, and determine underlying anatomy, and muscle motion. The generation of an anatomical model may be enhanced using known Eulerian capture techniques. In some embodiments, the patient head is scanned multiple times while specific facial expressions are exercised. For example, the expressions may involve smiling, frowning, yawning, shrugging, laughing, resting, among others. The resulting scans are processed to identify the underling muscles positions and actions. The muscle information may be used as an input to injection aid system 100, 400 that refines the medication injection schedule. The patient can be scanned after an injection procedure to obtain a treatment assessment and a calibration of medication sensitivity. This calibration may be used as input to calibrate subsequent treatment procedures.

Figure 6B:
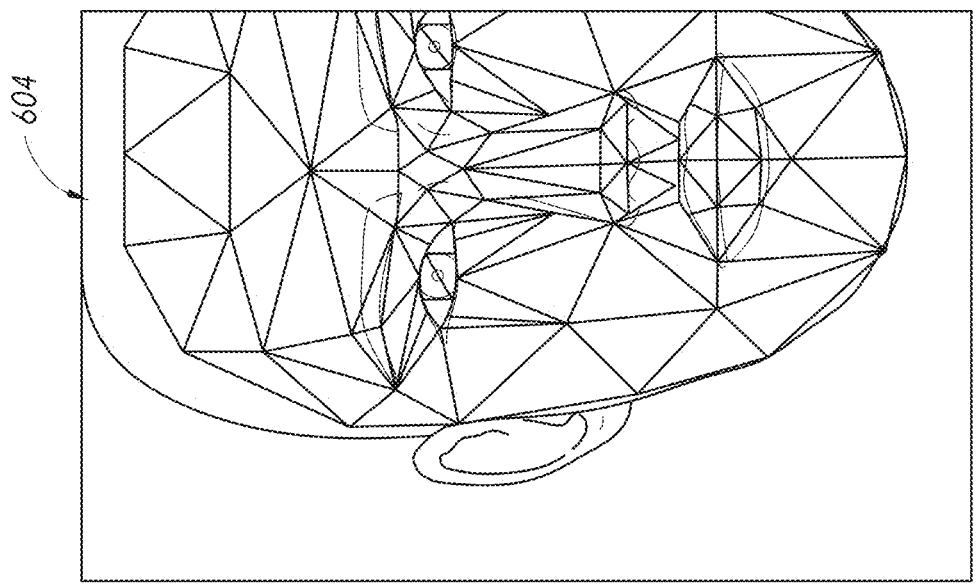
FIGS. 6A and 6B illustrate the use of computer vision to spot a treatment target based on contrast patterns typically seen in and around a human face.
Figure 6A:
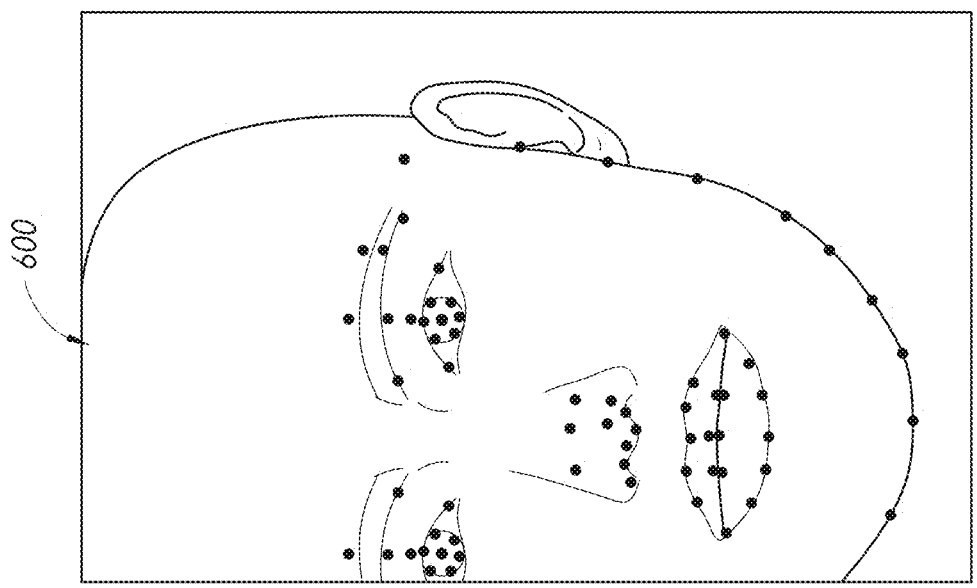

The injection aid system 100, 400 may incorporate psi and beauty optimization. In some embodiments, the injection aid system 100, 400 processes information from multiple scans of the patient and generates guidelines for improving patient beauty based on symmetry, balance, and phi ratios. Filters, such as, by way of non-limiting example, those utilized by Snapchat of Snap Inc., may be incorporated into the injection aid system. In some embodiments, the injection aid system 100, 400 uses computer vision to spot a user based on contrast patterns typically seen in and around a human face. FIG. 6A illustrates an example point-mask 600 generated to identify contrast patterns around a face. To obtain specificity as illustrated in FIG. 6A, the injection aid system 100, 400 may be trained using multiple faces manually marked with points to show where certain anatomical features reside. The injection aid system 100, 400 may generate a baseline point-mask 600 from the manually-marked faces, as illustrated in FIG. 6A. For example, the anatomical features may include the borders of lips, eyes, nose, and face. The injection aid system 100, 400 may incorporate the baseline point-mask 600 to individual patients and alter the baseline point-mask 600 to generate a patient-specific point-mask 600 matching the patient's face. The injection aid system 100, 400 may create a mesh 604 from the point-mask 600. FIG. 6B illustrates an example mesh 604. The mesh 604 may be capable of moving in accordance with a corresponding target movement. The mesh 604 may trigger a response when the target engages in particular activity, such as blinking, smiling, opening or closing its mouth, among other actions.

The injection aid system 100, 400 analyzes the patients scanned information and generates a set of treatment options with the intent to improve the psi ratio, in some instances. The injection aid system 100, 400 may develop an escalating sequence of treatments from minor facial injection through major facial surgery with an estimated psi ratio value for each level of treatment.

In some embodiments, the injection aid system 100, 400 calculates phi for facial injections to determine what the patient's face would look like with phi calculations. The injection aid system 100, 400 may apply phi calculations to a patient's face. The injection aid system 100, 400 may include having the phi calculations create a heat map detailing at least one of injection points, angles, and an amount of product to disperse. The injection aid system 100, 400 may recalculate the phi calculations following each injection to determine whether a proper injection occurred. The injection aid system 100, 400 allows the user to see the patient and view the calculations as applied to the generated heat map. The display device 108, 408 may include capabilities to permit the user to view the patient's current face alongside the patient's altered face following a phi calculation.

In some embodiments, the patient face is scanned frontally with a scanner. Once the frontal image is collected, the patient may then turn his or her head slowly to a first side, and then to the opposite side such that the scanner can obtain data to be used to construct a 3D image of the front portion of the patient's head. Scanning of a patient's face or other portion of the patient's anatomy may also be performed using other technologies such as MRI or CAT scans. Data from a previous scan may also be used if it exists.

Figure 7:
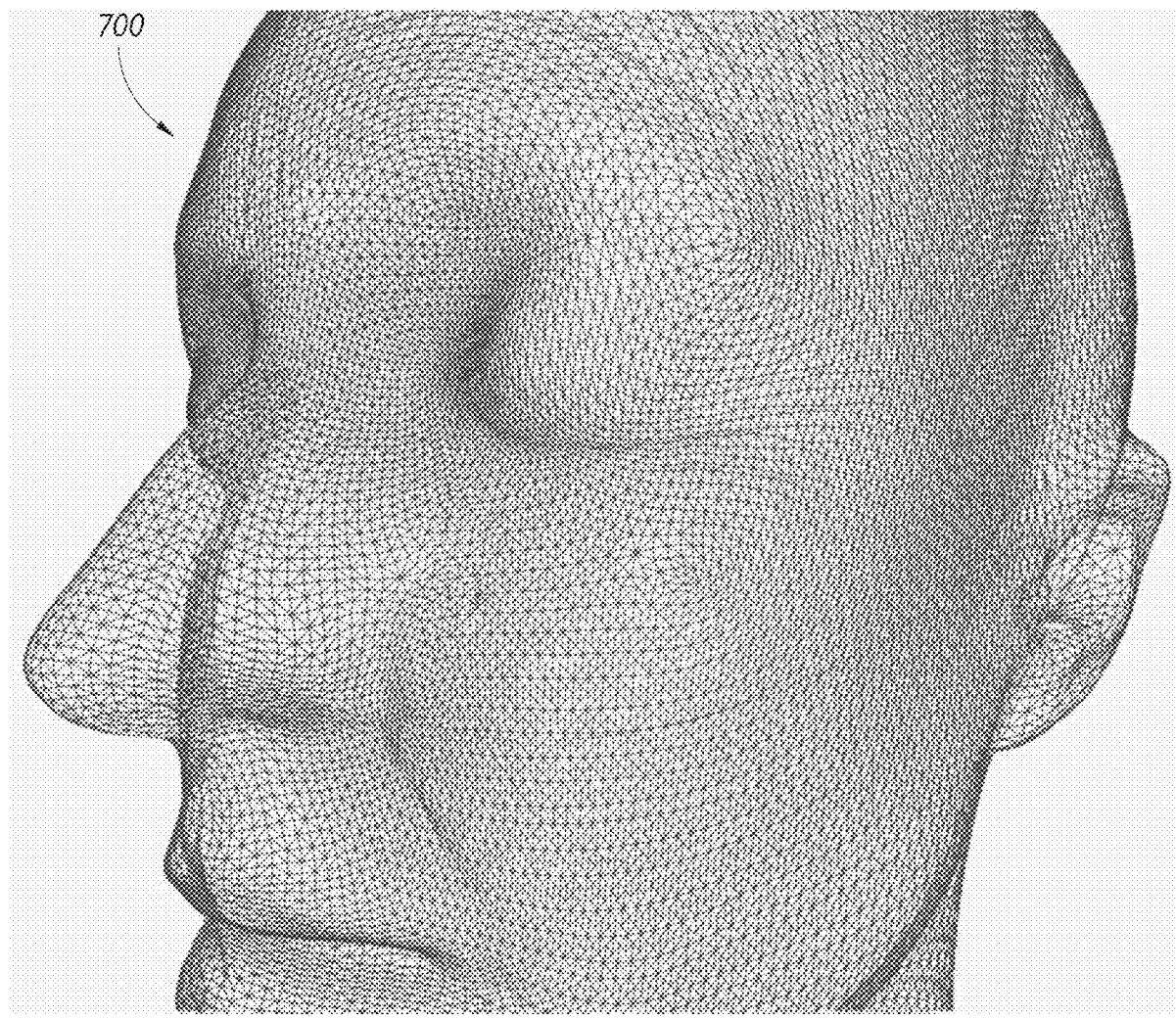
FIG. 7 illustrates a model mesh used to represent the facial skin of a treatment target.

In some embodiments, a patient's face or other portion of the patient's anatomy may be derived mathematically by extracting a 3D model of patient's exterior surface geometry. Generation of the model may also include extracting the locations of bone, fat pads, nerves, muscles, and blood vessels from scan data. The location data from the scan can be converted to a series of polygons 700 in 3D space, representing the boundaries of each feature. For example, as illustrated in FIG. 7, a series of polygons 700 may represent the outside skin of the patient. Infrared technology may be used to perform mapping of blood vessel locations in the patient's anatomy. CT scans or other such scanning technology capable of identifying anatomical tissues or structures below the surface of the body (for example, beneath the skin, muscle, etc.) may be used to provide information to support modeling of below-the-surface anatomical characteristics.

Having collected data representative of the patient's anatomy, the disclosed systems, devices and methods may be used to render polygon-based objects as a model mesh 700 of the patient, as illustrated in FIG. 7. The model mesh 700 may include a three-dimensional structure including a series of polygons representing different features of the patient, such as bone, blood vessels, fat pads, muscles or nerves. These series of polygons may be rendered in different colors or with different graphical textures to make them distinct from each other or to match anatomical coloring. The resulting model mesh 700 may be rotated, zoomed and manipulated in ways such as, for example, removing layers to make interior features visible. This interactive model mesh 700 can be used for general aid during a medical procedure and/or training to permit the user to better understand the patient's specific facial anatomy, specific procedure planning, and visually demonstrating to patients what they might look like after a procedure.

In an embodiment the injection aid system 100, 400 and the patient's anatomy can be combined and displayed using a holographic or pseudo-holographic projector. The user can interact with the projection directly with a physical or virtual syringe. The injection aid system 100, 400 can use ultrasonic projectors to sense the location of the hand, as well as provide haptic feedback similar to existing systems.

According to an embodiment of the present disclosure, at each time step of a simulated and/or actual injection, the amount of therapeutic product injected at the location of the needle tip is estimated using the product of the plunger force (as measured by a force sensor in the syringe) and the time interval the plunger is depressed. This number is scaled by a predetermined constant, K, appropriate to each therapeutic injection product, to approximate the amount of therapeutic product injected at each location. Thus:

$$\text{Force}_{(plunger\ depressed)} \times \text{Time}_{(plunger\ depressed)} \times K_{(product\ constant)} = \text{Product Amount Injected}_{(estimated)}$$

The predetermined constant, K, relates the therapeutic product dispensed to the plunger force and duration of time exerted. The constant, K, for a particular therapeutic product is affected by external factors including viscosity of the product and the prescribed needle type and dimensions. The constant, K, can be determined via real world measurement and may be uniquely determined for each therapeutic product type that is simulated.

Predetermined targets 424 for product delivery can be identified by a target 3-dimensional location, a larger allowable "sphere" around the target 424 location, and the allowable range of therapeutic product injection amounts. The user is instructed as to the region and/or set of target points on which to perform the procedure, as well as the amount of therapeutic product to be injected.

Figure 8:
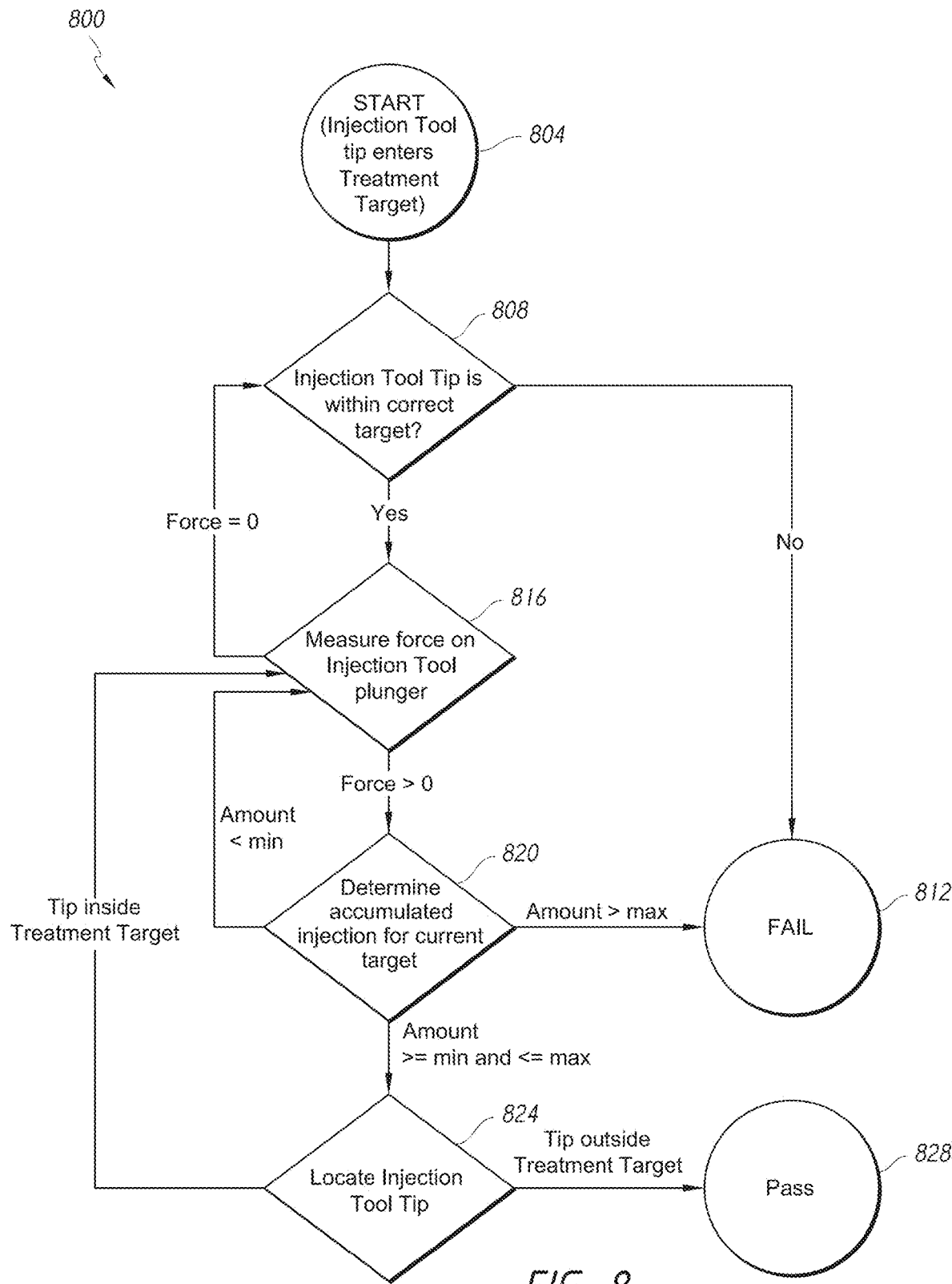
FIG. 8 is a flow diagram describing a process for scoring a single, non-filler injection.

In an embodiment, there are two main types of injection sequences: filler and non-filler. A process flow for scoring a single non-filler injection 800 in accordance with an embodiment of the present disclosure is shown in FIG. 8. At step 804, the user interacts with the injection tool 112, 412 to insert the injection tool 112, 412 into the treatment target 116, 416. At step 808, the injection aid system 100, 400 determines if a tip of the injection tool 112, 412 is located within a correct target 424 (as shown in FIG. 4) in the treatment target 116, 416. If the injection tool 112, 412 is not located within the correct target 424, the injection aid system 100, 400 proceeds to step 812 and determine that the process failed. If the injection tool 112, 412 is located within the correct target 424, the injection aid system 100, 400 proceeds to step 816.

At step 816, the injection aid system 100, 400 measures the force applied to a plunger of the injection tool 112, 412. If the measured force is greater than zero, the process proceeds to step 820. If the measured force is less than zero, the process proceeds back to step 808.

At step 820, the injection aid system 100, 400 determines an accumulated injection for the current target. If the accumulated amount is greater than a target minimum and less than a target maximum, the process moves to step 824. If the accumulated amount is less than a target minimum, the process proceeds back to step 816. If the accumulated amount is greater than a target maximum, the process moves to step 812 and determines the process failed.

At step 824, the injection aid system 100, 400 locates the tip of the injection tool 112, 412. If the tip is located within the treatment target, then the process moves back to step 816. If the tip is located outside the treatment target, the process moves to step 828 and determines the process passed.

Figure 9:
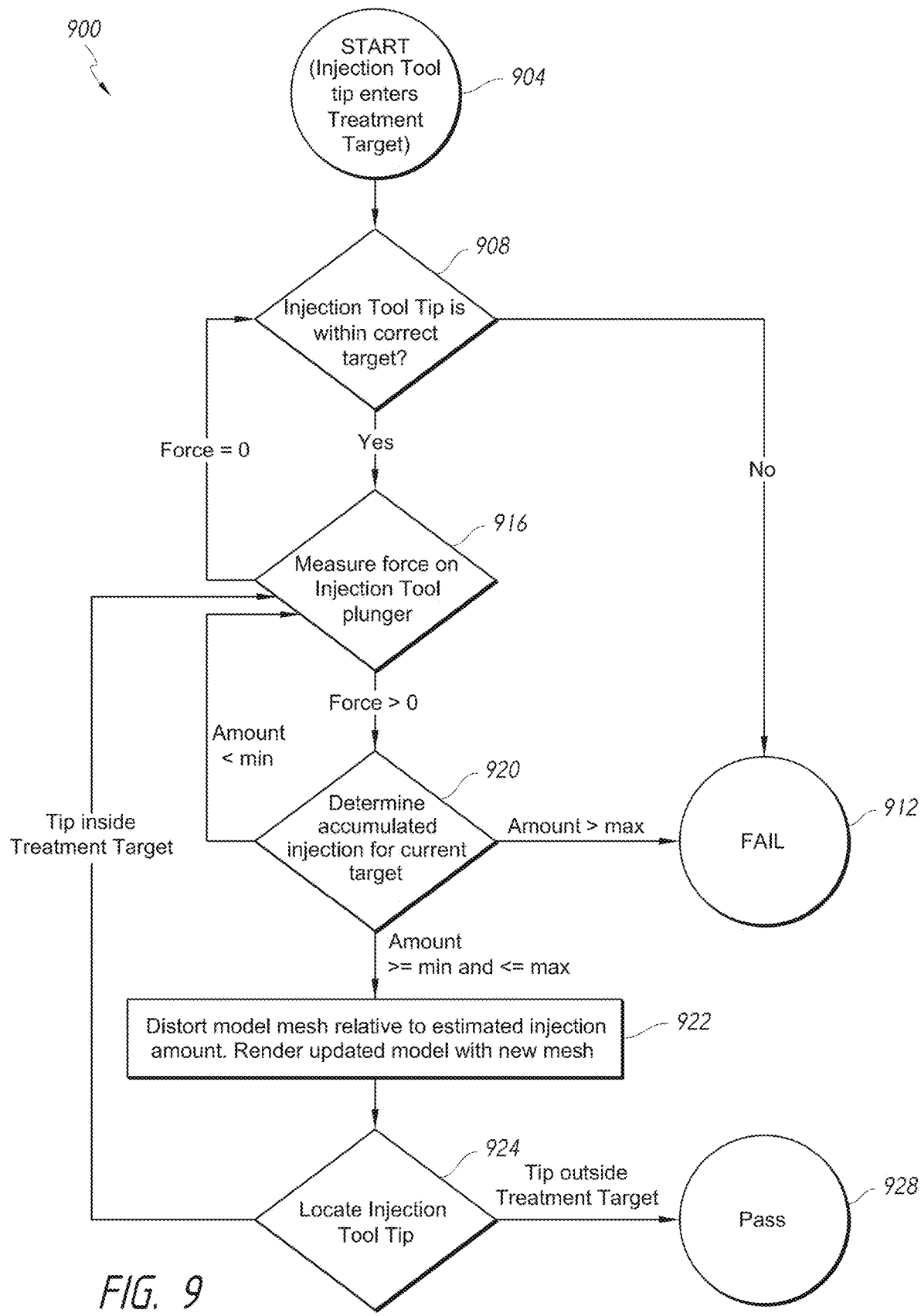
FIG. 9 is a flow diagram describing a process for scoring a filler injection.

A process flow for scoring a filler injection 900 in accordance with an embodiment of the present disclosure is shown in FIG. 9. The process flow 900 resembles or is identical to the process flow 800 except with the addition of step 922. Accordingly, numerals used to identify features of the process flow 900 identify like step of the process flow 800 incremented by a value of 100.

At step 922, the injection aid system 100, 400 distorts the modal mesh relative to the calculated estimated injection amount and renders the updated model mesh with the new mesh. The process then continues to step 924.

Determining if a product is within an injection target may be performed using geometric calculations from the measured tip position of the injection tool 112, 412. For example, each target location may be a sphere with a certain radius, or a cone or cylinder.

During the course of the above-described sequence 800, 900, the position of the injection tool 112, 412 and its needle tip is represented in the interactive model mesh 700. The user can manipulate the model mesh 700 during the course of the sequence 800, 900 at any step.

The measured locations and forces can be recorded and played back to the user, with the playback being able to be paused, replayed or changed in speed. Additionally, users can peel back layers, zoom in, change perspective on the model mesh 700 and the injection playback, while playback is occurring.

To visually show impact of filler injections, the act of distorting the model mesh 700 in response to filler product can be embodied in a variety of ways. In an embodiment, the nearest vertices of the model mesh 700 are moved away from the location of the needle tip by an amount proportional to the amount of therapeutic product injected. This may be performed by moving the closest few vertices outward along the face normal (i.e., perpendicular) to the skin surface and proportional to face size. This has the effect of increasing the volume under the skin by the volume of the filler added. According to another embodiment, the system tracks a number of tiny spheres and moves the spheres around in response to injections under the skin using fluid flow modeling methods known to the art. The model mesh 700 can be modified in response to the pressures predicted by such a model. In another embodiment, pre-drawn models where both the model mesh 700 and also the colored and textured skin have been created to show a certain amount of change in response to filler being added in a certain area. A pre-drawn model corresponding to the present circumstances is selected based on the total amount of filler injected into a certain target. The program may additionally create intermediate representations of the model mesh 700 and skin by averaging two adjacent models.

Computing System for Injection Aid Systems

Figure 10:
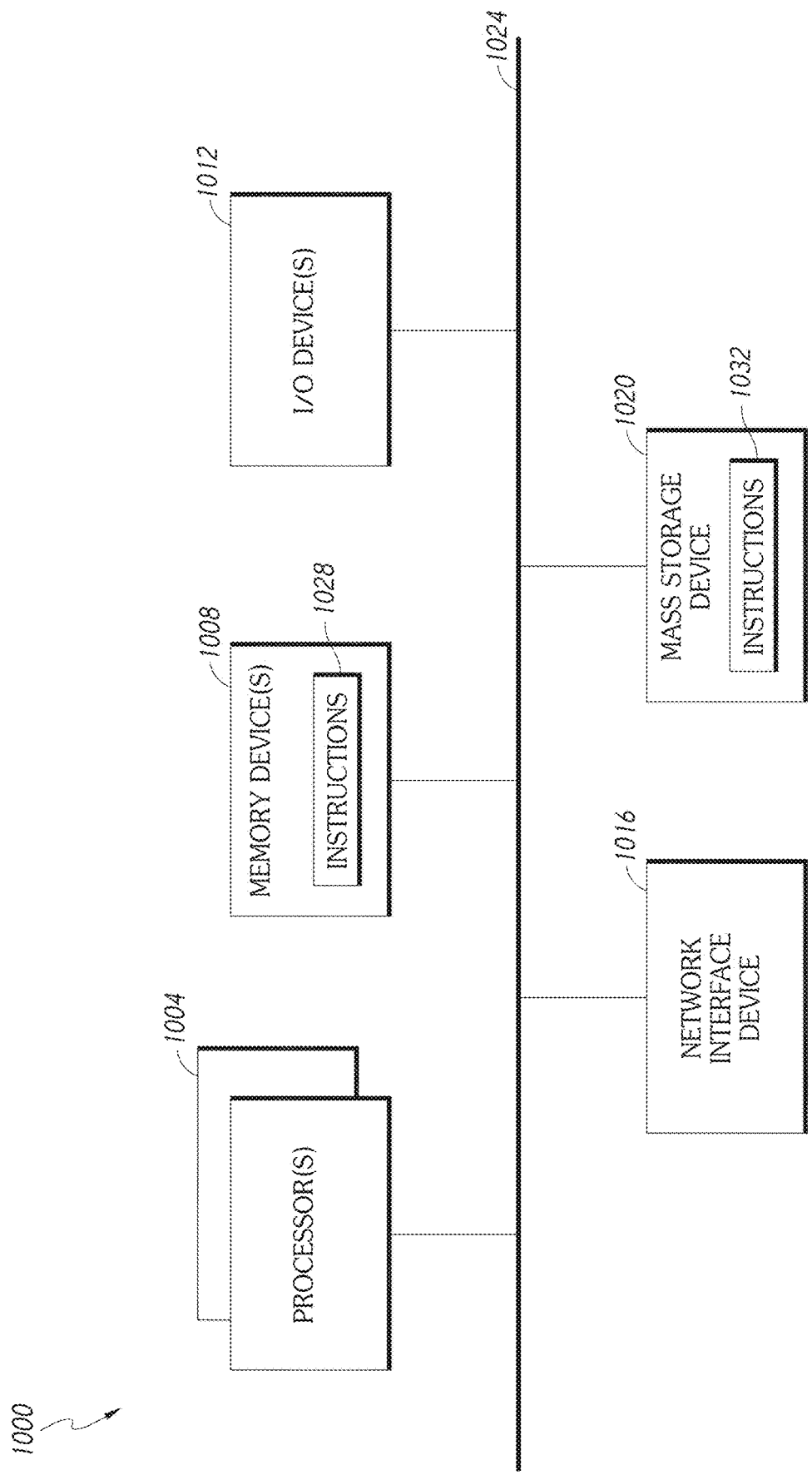
FIG. 10 is a functional block diagram of an example general purpose computer system suitable for use in the disclosed aid systems and for executing the disclosed methods for the aid systems.

In some embodiments the disclosed injection aid system 100, 400 comprises a computing system. FIG. 10 is a functional block diagram of an embodiment of a general purpose computing system suitable for use in implementing the disclosed systems and in executing the disclosed methods and the executable instructions stored on the non-transitory, computer-readable media for injection training in accordance with various embodiments of the present disclosure. By way of illustration, the computing system includes a computing device 1000. The computing device 1000 can take one or more of different forms, including, by way of non-limiting examples, a laptop computer, a stand-alone personal computer, a server, a tablet, a workstation, a handheld device, a mobile device (such as a smartphone), and a consumer electronic device (such as a video game console), to name a few. The computing device 1000 can be a stand-alone device, or it can be configured to be part of a computing network, a computing cluster, a cloud-based computing infrastructure, or the like.

In a basic configuration, the computing device 1000 can include one or more processors 1004 and one or more memory devices 1008. The one or more processors 1004 can be configured to execute instructions and to process data to perform one or more functions, such as the methods and the executable instructions stored on computer-readable media disclosed herein. Illustratively, the one or more processors 1004 may include, without limitation, two or more processing cores on a single processing chip, two or more separate processor chips, or both. In some embodiments, the computing device 1000 can also include one or more additional or specialized processors such as, for example, a graphics processor (not shown), to perform graphics processing functions that can be diverted from the one or more processors 1004 to improve performance and/or to relieve their workload. The memory 1008 can be arranged in a hierarchy and can include one or more levels of cache. The memory 1008 may include one or more memory devices that store data, including without limitation, volatile memory such as random access memory (RAM), non-volatile memory, such as and read-only memory (ROM), flash memory, etc., or a combination of volatile and non-volatile memory.

The computing device 1000 can also include one or more input and output (I/O) connections, such as USB connections, display ports, proprietary connections, and others to connect to various devices to provide inputs and outputs to the computing device 1000. The I/O device(s) 1010 may include one or more components that allow a user of the computing device 1000 to interface with applications executing in the computing device 1000. For example, the I/O device(s) 1010 may include devices such as a keyboard, a mouse, a touch pad, a touch screen, a microphone, an accelerometer, a camera, or any other user input device configurable to work with the computing device 1000. The I/O device(s) 1010 may also include, for example, a display (e.g., an LCD display, a CRT display, an electronic ink display, or a plasma display, to name a few), a printer, a speaker, or any other output devices configurable to work with the computing device 1000.

The computing device 1000 can also include one or more network interface devices 1014 that allow the computing device 1000 to communicate with other computers and applications. The one or more network interface devices 1014 may include any communication device for sending and receiving data across a network, including but not limited to, a network interface card, a modem, or another network adapter capable of transmitting and receiving data over a network. Communication protocol connections can include, without limitation, an Ethernet interface, a wireless interface, a bus interface, a storage area network interface, and a proprietary interface. Communication connections established via the network interface devices 1010 can be used to connect the computing device 1000 to a computer network. A computer network is a telecommunications network that enables computers, and possibly other devices, to exchange data and share resources along data connections. There are many different types of computing networks that exhibit a variety of characteristics such as topology, connection method, and scale. Examples of computer networks include a local area network, a wide area network, the Internet, or other networks.

The computing device 1000 can also include one or more mass storage devices 1018. The one or more mass storage devices 1018 can be removable or non-removable, and can include, without limitation, a magnetic storage device (e.g., a hard disk), an optical storage medium (e.g., a compact disc (CD) drive or a digital versatile disc (DVD) drive), a high-definition optical storage medium, an electronic storage device (e.g., an erasable programmable read-only memory (EPROM) or a flash drive), solid-state memory, flash storage devices, or other data storage devices known in the art. Computer storage media can include volatile, non-volatile, removable, and non-removable media configured to store information such as, for example, computer-readable instructions, data arrangements, program components, or other information. Illustratively, computer storage media can include, without limitation, random access memory (RAM), read-only memory (ROM), electrically erasable programmable read-only memory (EEPROM), flash memory, solid-state memory, CD-ROM, DVD memory, or other optical storage, magnetic cassettes, magnetic tape, magnetic disk storage or other magnetic storage devices, a universal serial bus (USB) flash drive, a flash memory card, or other flash storage devices, or any other storage medium that may be configured to store computer-readable information and that can be read by the computing device X00. The one or more memory devices 1008 and the one or more mass storage devices 1018 may be employed to store a working copy and a permanent copy of programming instructions, illustrated as instructions 1026 and 1030, respectively, for implementing various aspects of the embodiments of the present disclosure. The components of the computing device 1000 can be coupled together by way of a bus 1022, which may represent one or more buses.

System for Social Aid

FIGS. 11-16C show an embodiment of a social aid system. The social aid system resembles or is identical to the injection aid system 100, 400 discussed above except as described differently below. Accordingly, numerals used to identify features of the social aid system shown in FIGS. 11-16C identify like features of the injection aid system shown 11, 400 in FIGS. 1-10. The foregoing descriptions can be combined with the specific discussion below in other various embodiments.

The disclosed systems and methods can be directed towards a social training system. There is a population of humans with reduced capacity to read social cues. This population includes persons with varying degrees of autism spectrum disorder. The social aid system may assist these individuals with developing the ability to read social cues. By way of non-limiting examples, the social aid system may assist in detecting social cues including facial expressions, facial color, facial motion, body language, voice tones, speech pace, and buried frequencies, along with other signals. The social cues may involve rules for interaction with other individuals, recognition of behaviors that predict social outcomes, and a determination of another's cognitive and language skills. Missing or misinterpreting these social cues can be harmful. The social aid system may provide a means to assist individuals with learning these social cues.

Figure 11:
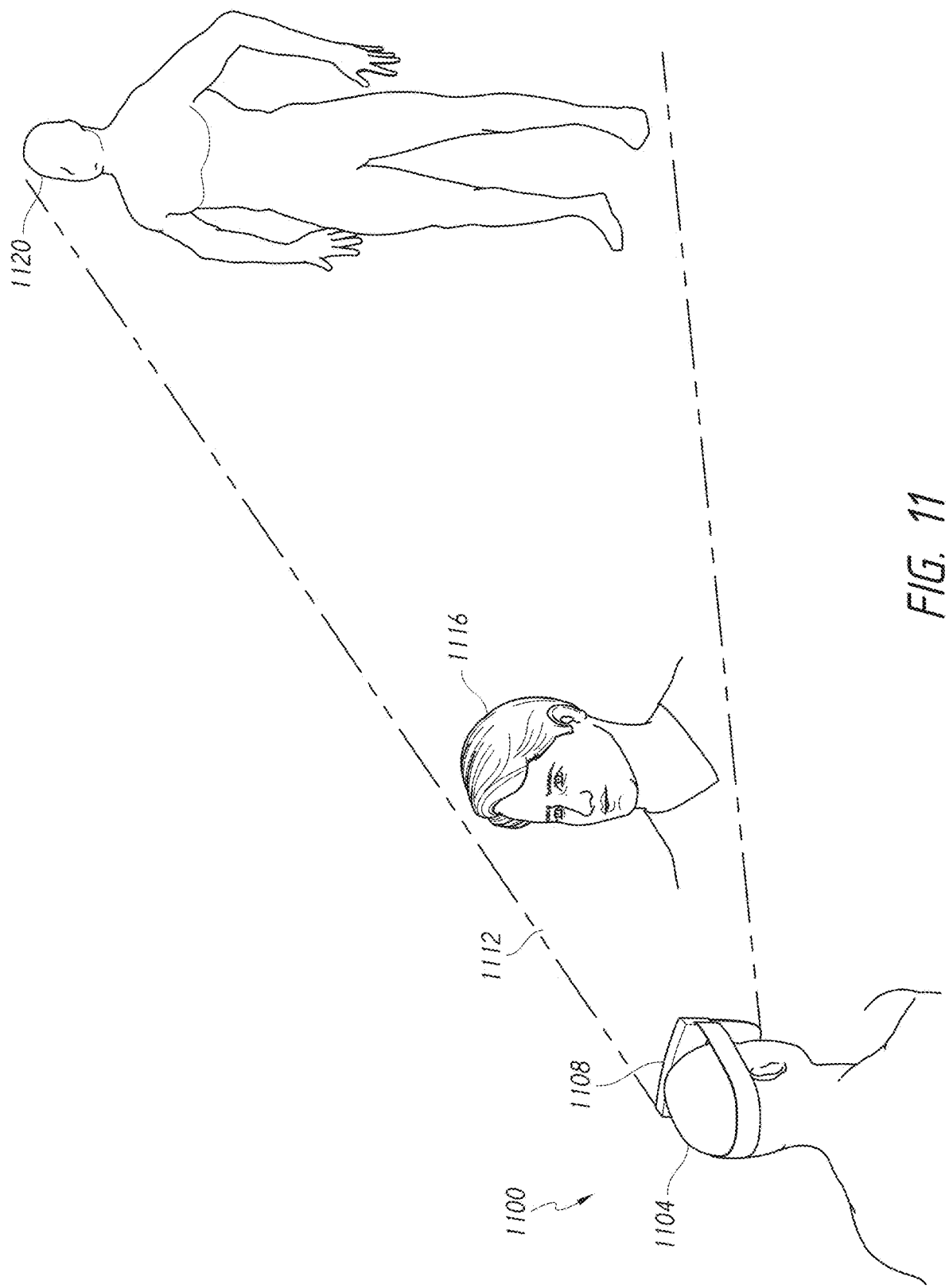
FIG. 11 illustrates a social aid system according to one embodiment herein.

Similar to the injection aid systems 100, 400 described herein, FIG. 11 illustrates social aid system 1100 configured to generate a virtual environment in which a user may be engaged. In one embodiment, the social aid system 1100 comprises a display device 1108 configured to present visual images of the virtual environment to the user 1104. The display device 1108 may be coupled to a computing system and configured to present visual images generated by the social aid system 1100. The social aid system 1100 may use information available to a user 1104 to provide the user 1104 with more complete and accessible information. The information may advantageously result in more informed treatment procedures and superior outcomes.

The social aid system 1100 may utilize augmented reality, similar to the injection aid system 400, to provide an opportunity to overlay a variety of information in the form of words, symbols, pictures, and/or video into the field of view 1112 of the user 1104. A user 1104 can wear the social aid system 1100, while continuing to view the actual environment though a clear lens 1211 (shown in FIG. 12) of the display device 1108. In some embodiments, the social aid system 1100 is configured to project a wide array of information onto the display device 1108 through multiple formats. For example, display formats include an image projected at a location offset from the user's direct line of sight. In this way, the information is visible to the user 1104 while not obstructing the field of view 1112 of the user 1104. This information may appear to float in space. In some embodiments, the social aid system 1100 projects information at a location directly overlaying the field of view 1112 of the user 1104. The information may then appear to be projected onto a surface being viewed. A surface being viewed may include a human face, in some instances. In some embodiments, information can be conveyed to the user 1104 by means of audio or tactile signal to the user 1104.

The social aid system 1100 may detect particular social cues depending on the location of an individual present in the field of view 1112 of the user 1104. In some embodiments, the social aid system 1100 acquires information on at least one of the facial expressions, facial color, facial motion, body language, voice tones, and speech pace of a close-range individual 1116. The social aid system 1110 may acquire information on at least one of the body language, environmental sounds, movement pace, and body stance of a far view individual 1120.

Figure 12:
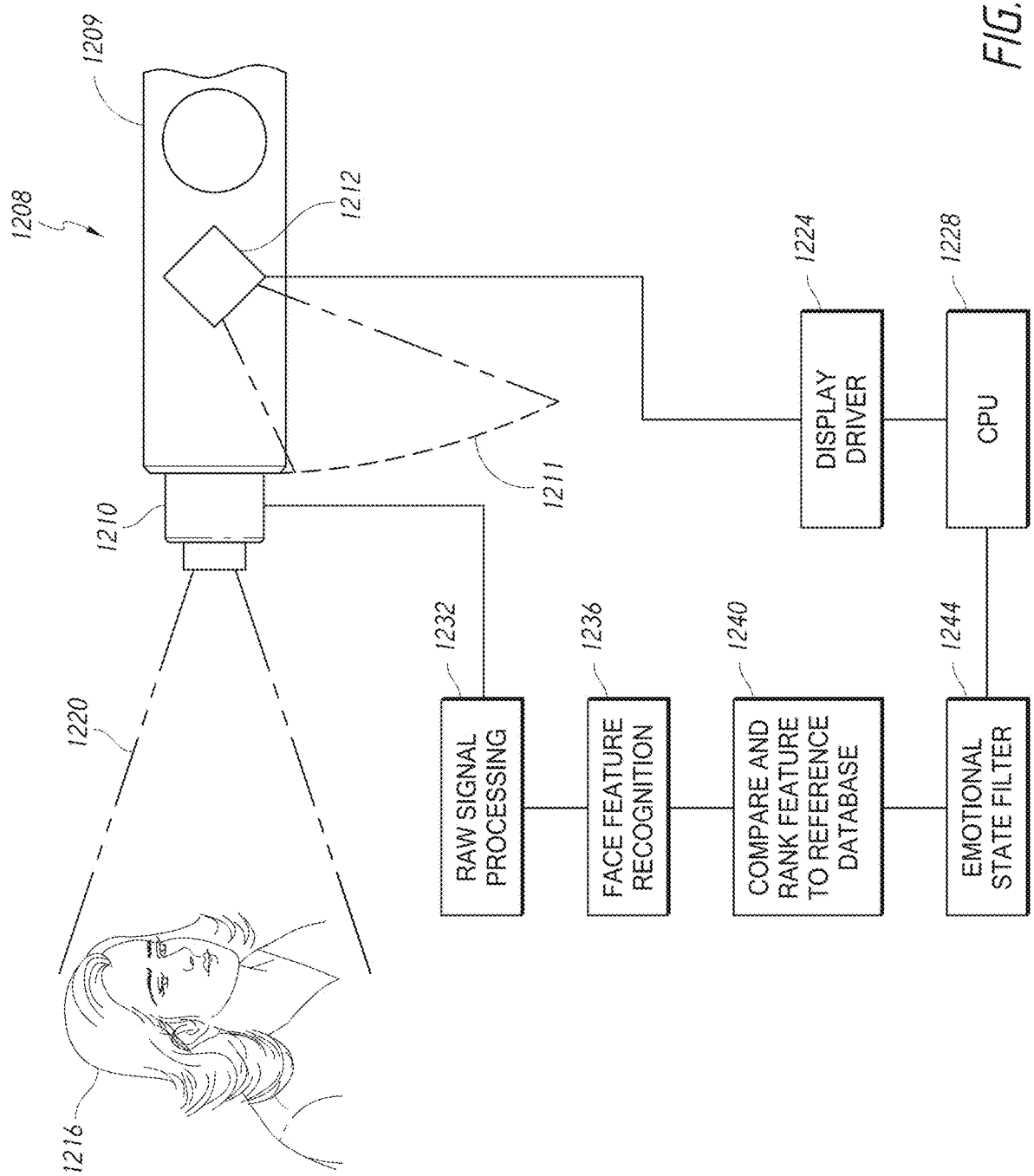
FIG. 12 illustrates an example social aid system suitable for executing the disclosed methods for social training.
Figure 13:
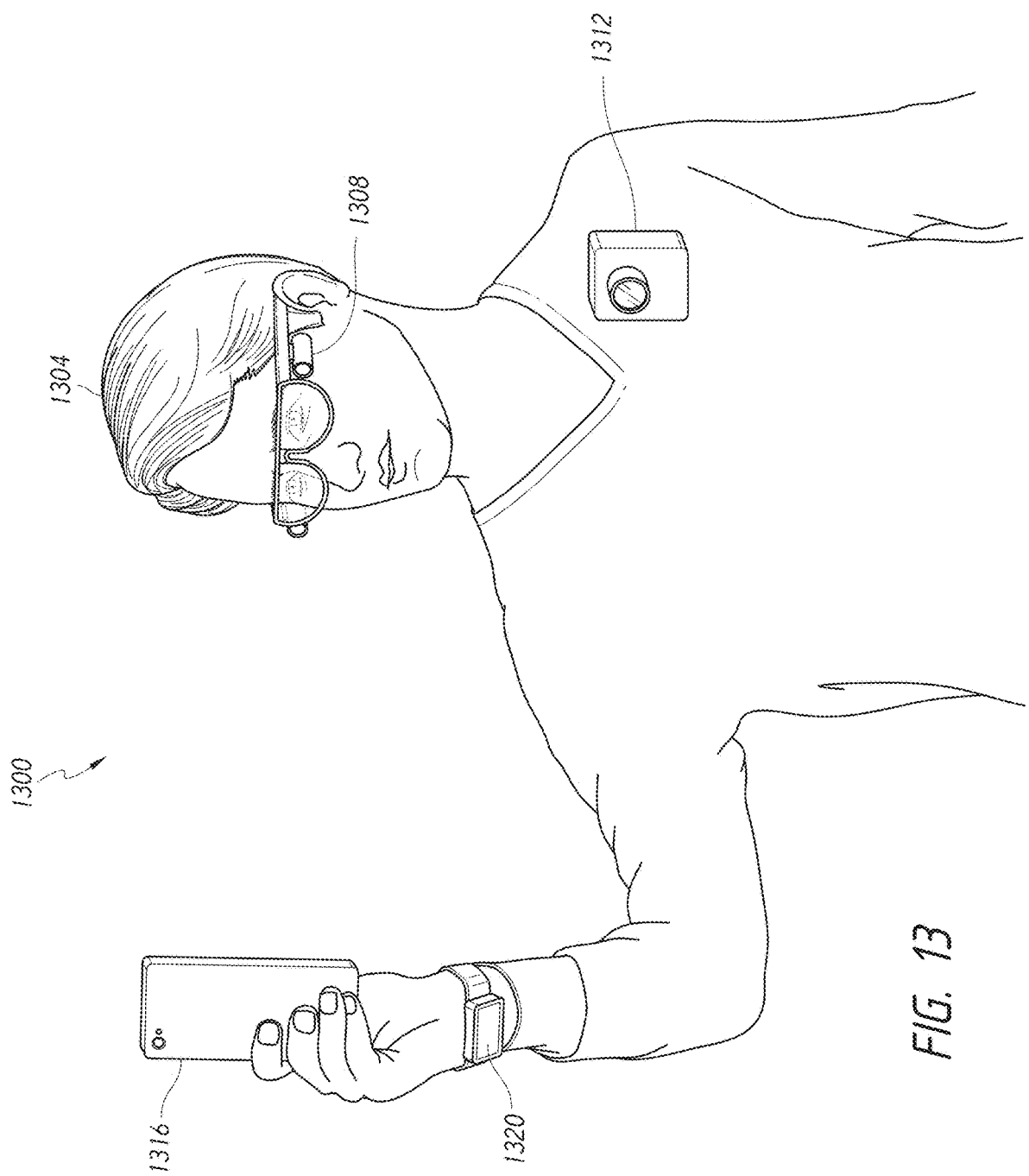
FIG. 13 illustrates various embodiments of the social aid system of FIG. 11.

FIG. 12 illustrates an embodiment of the social aid system 1200 comprising a display device 1208 including a head band 1209 to secure the device on a user's head. The display device 1208 may include a visor lens 1211 and a projector 1212 capable of projecting images onto the visor lens 1211. In some instances, the display device 1208 comprises a scanner 1210. The scanner 1210 is configured to track facial expressions, collect multiple high-resolution scans, and/or detect various features of a human being 1216 in the field of view 1220 of the user, such as the social cues described above. FIG. 13 illustrates various embodiments of the scanner. The scanner may include a camera 1308 clipped on or built on an eyeglass. The scanner may comprise a lapel camera 1312 attachable to various articles of clothing worn by the user 1304. In some embodiments, the social aid system 1300 incorporates the use of a mobile device 1316 and/or a wearable device 1320 to acquire information relating to an observed individual. The social aid system 1100 may utilize the information acquired by the scanner 1210 to generate anatomical models and/or social models of an observed human 1216. The scanner 1210 may detect relative position of at least one individual 1216 in the field of view 1220 of the user 1104. The social aid system 1100 may detect social cues information and process the information into variety of outputs designed to improve a user's social understanding. In some embodiments, the social aid system 1100 includes a computing system. The computing system is configured to process social cue information and generates a virtual environment. The display device 1208 may be coupled to the computing system and configured to present visual images depicting the virtual environment generated by the social aid system 1100. The computing system incorporates the social cue information into the virtual environment displayed to the user. As described above, the social aid system 1100 may include a display device 1208 to measure the social cues of various individuals 1216 in the user's field of view 1220. The display device 1208 may communicate the information to the computing system, such that the social cue can be displayed in the virtual environment.

As illustrated in FIG. 12, the computing system may include at least one of several components: a display driver 1224, a central processing unit 1228, a raw signal processor 1232, a facial feature recognition 1236, a compare and rank feature capable of referencing to a database 1240, and an emotional state filter 1244. One or more of the listed components may be utilized by the computing system to process the information received by the social aid system 1100 and generate information on the display device 1108 in a format readily understandable by the user 1104. For example, the computing system may assess the emotional state of an observed individual 1216. The social aid system 1100 may then project an appropriate symbol onto the display device 1108 to be viewed by the user 1104. Additional information regarding the computing system is disclosed above. FIGS. 14A-15B show embodiments of anatomical models generated by the social aid system 1100. The anatomical models resemble or are identical to the anatomical models discussed above except as described differently below. Accordingly, numerals used to identify features of the anatomical models shown in FIGS. 14A-15B identify like features of the anatomical models shown in FIGS. 6A-7. The foregoing descriptions can be combined with the specific discussion below in other various embodiments.

Figure 14C:
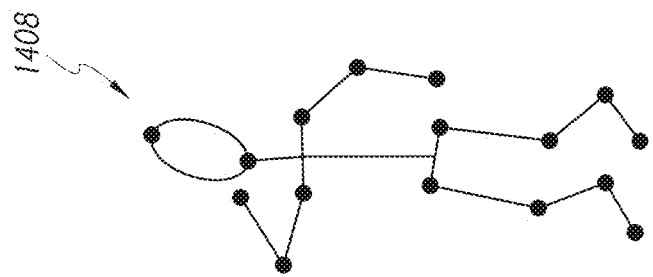
FIGS. 14A through 14C illustrate the use of computer vision to spot a target behavior based on contrast patterns typically seen in and around a human stance.
Figure 14B:
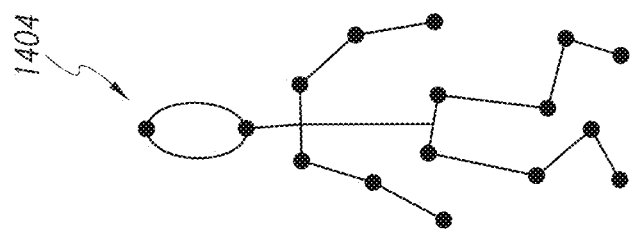
Figure 14A:
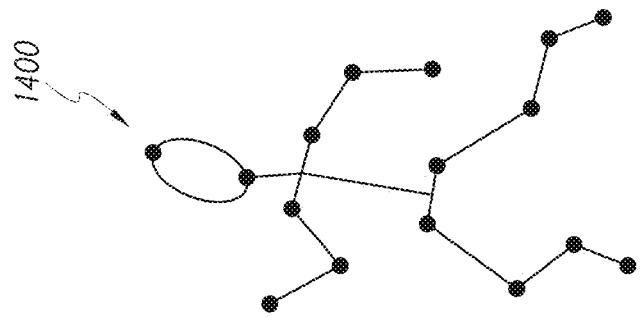
Figure 15B:
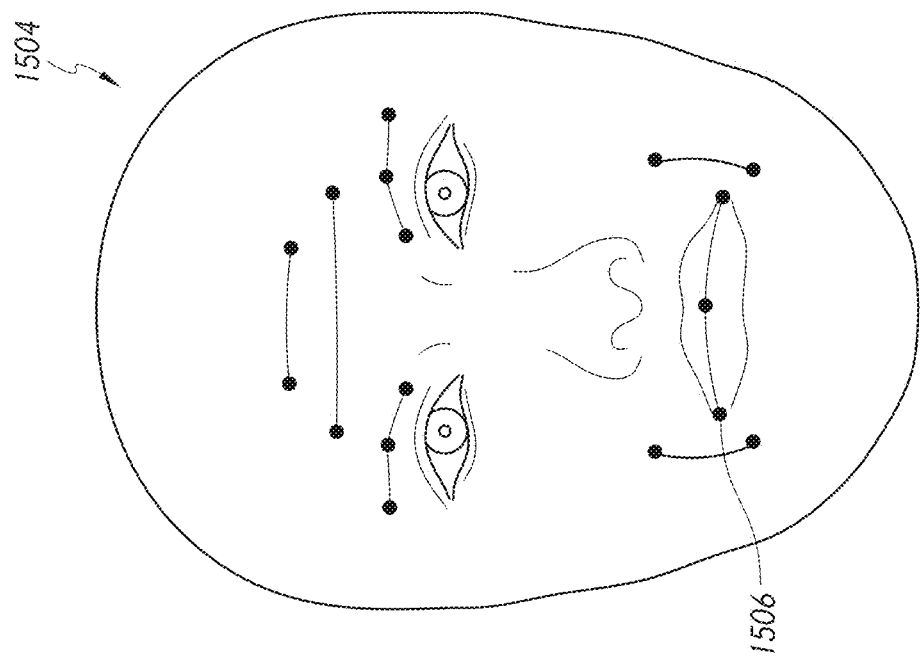
FIGS. 15A and 15B illustrate the use of computer vision to spot a target behavior based on contrast patterns typically seen in and around a human face.
Figure 15A:
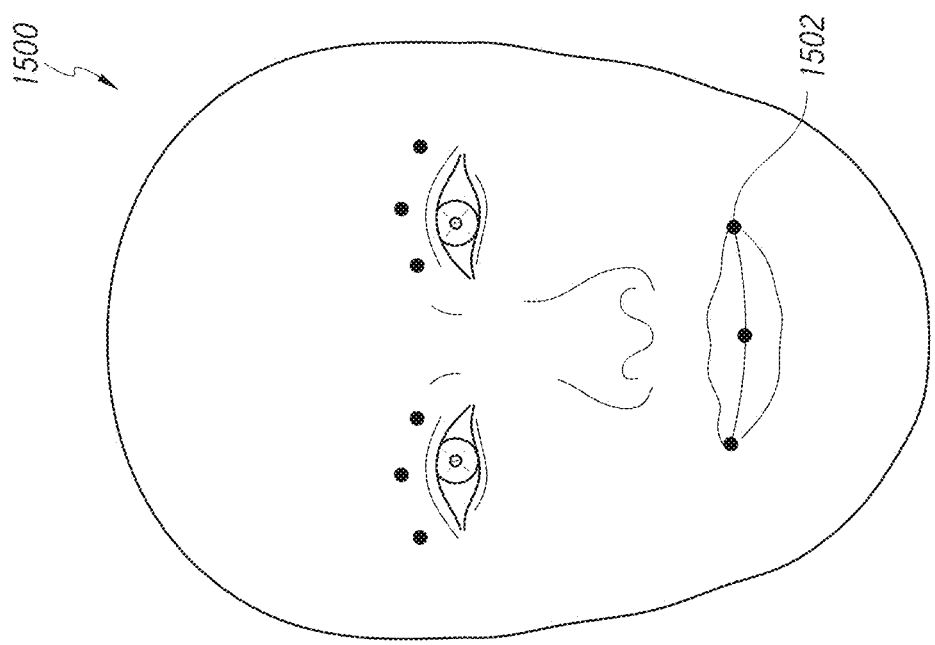

The social aid system 1100 may utilize various facial expression scans to develop a comprehensive mapping of an observed individual's facial expressions, facial color, facial motion, and body language to more accurately determine social cues. As illustrated in FIGS. 14A-C, the social aid system 1100 may utilize techniques described herein to determine an observed individual's stance. The stance may comprise one of a variety of categories, such as an approaching stance 1400, normal stance 1404, and wondering stance 1408. By way of non-limiting examples, several additional stance categories may include angry, threatening, waiting, sad, and worried, among others. Based on the determined stance, the social aid system 1100 may provide the user with information relating to the observed individual's social cues. Similarly, the social aid system may determine an observed individual's facial expression. FIG. 15A illustrates the social aid system's analysis of a "normal" facial expression 1500 utilizing a point-mask 1502, as described previously. FIG. 15B illustrates a similar analysis of a "mad" facial expression utilizing point-mask 1506. By way of non-limiting examples, several additional recognizable facial expressions may include laughing, crying, smiling frowning, yawning, and wondering, among others. As disclosed herein, the generation of the anatomical model(s) may be enhanced using known Eulerian capture techniques. In some embodiments, the observed individual is scanned multiple times to process and identify the underling social cues. This social cue information may be used as an input to social aid system 1100 to refines the social instruction provided to the user.

Figure 16A:
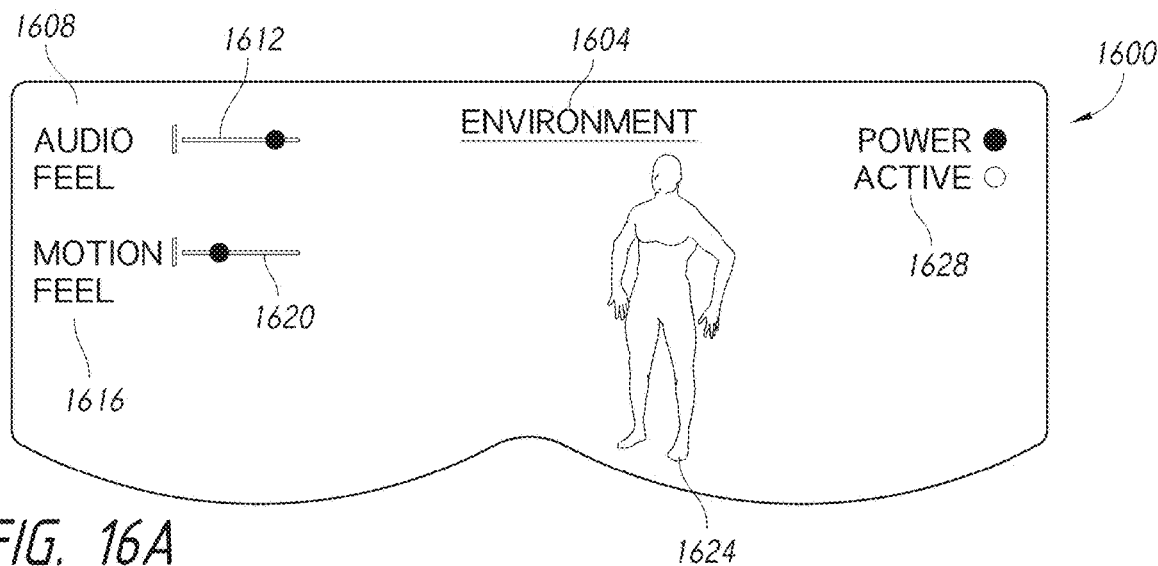
FIGS. 16A through 16C illustrate various embodiments of views appearing on a display device of the social aid system.
Figure 16B:
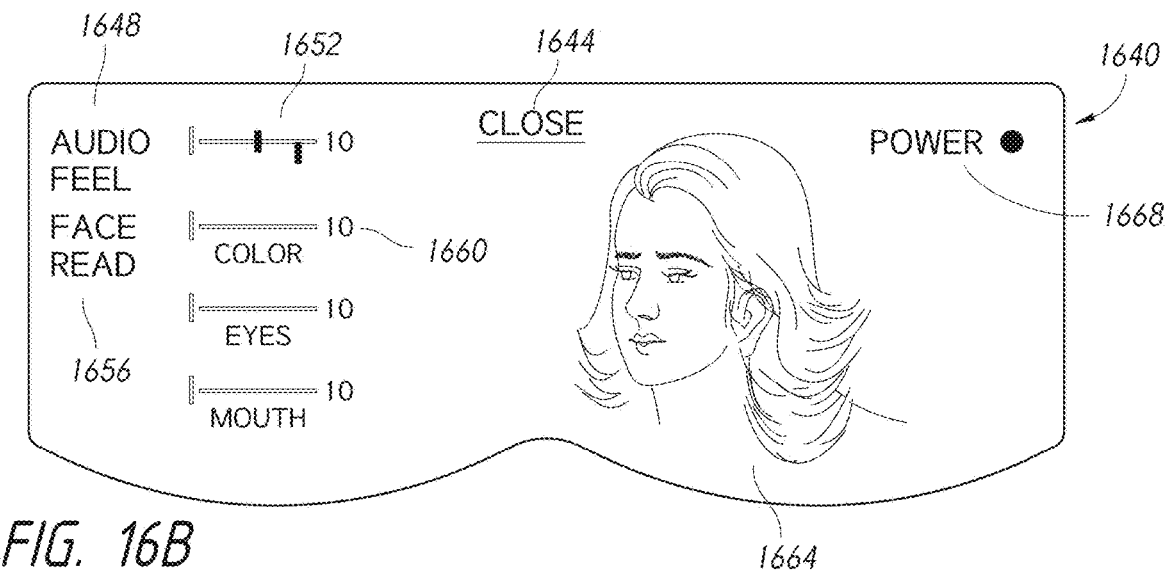
Figure 16C:
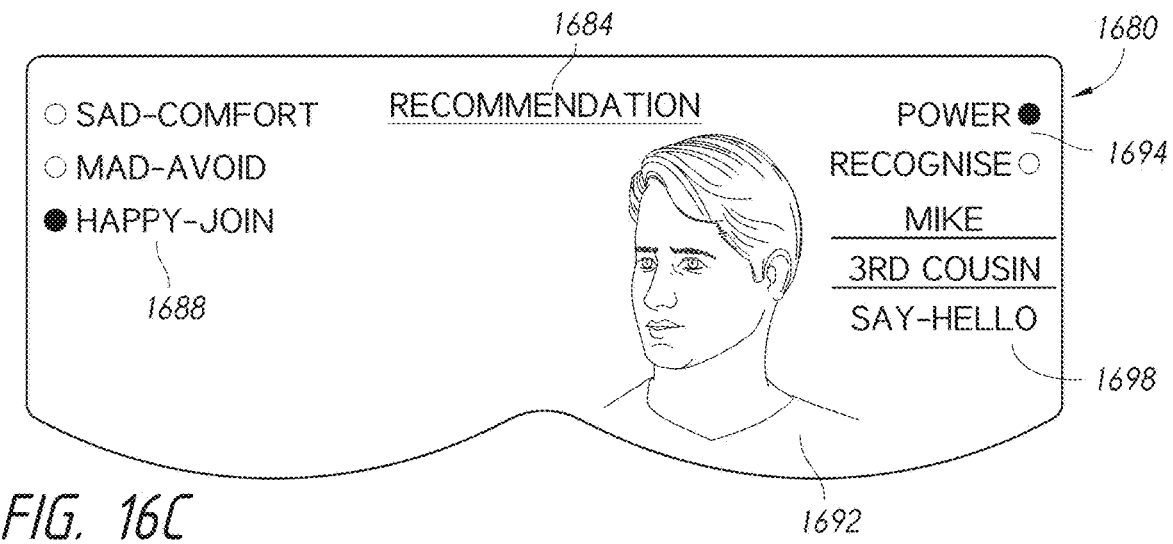

FIGS. 16A-C illustrate a various views of the display device 1108, 1208 that may selectively display information to the user 1104. By way of non-limiting example, the information projected on the display device 1108, 1208 may a power indicator, a proximity indicator, a determination of the observed individual's audio levels and/or motion levels, a view of the observed individual's determined emotional state, biographical information regarding the observed individual, suggested social responses, comparison of the user's social responses to optimum responses, and testing and scoring information, among other information. This information may be projected to appear in the field of view of the user 1104 and avoid the need to shift attention from observed individual. Information that may be present in all display views 1600, 1640, 1680 include a power indicator 1628, 1668, 1694 and a view of the observed individual 1624, 1664, 1692.

FIG. 16A illustrates one such display view containing information that can be seen on the display device 1108, 1208. The illustrated embodiment depicts a long range view 1600 that provides a general overview of the environment. As discussed above, the information could include the social cue information processed by the social aid system 1100, with color and or shape symbols coded to indicate various social aspects of an observed individual. The long-range view 1600 may indicate the proximity category of the observed individual. In the illustrated embodiment, the long-range view 1600 provides a long-range indication 1604 to the user. The long-range view 1600 may comprise an audio level 1608 determination of the observed individual and a corresponding visual representation 1612 of the audio level. In some instances, the long-range view 1600 may provide a similar analysis of a motion level 1616 determination of the observed individual with a corresponding visual representation 1620 of the motion level.

FIG. 16B illustrates another such display view containing information that can be seen on the display device 1108, 1208. The illustrated embodiment depicts a close-range view 1640 that provides information relating to a single person. The close-range view 1604 may indicate the proximity category of the observed individual. In the illustrated embodiment, the close-range view 1600 provides a close-range indication 1644 to the user. The close-range view 1640 may comprise an audio level 1648 determination of the observed individual and a corresponding visual representation 1652 of the audio level. In some instances, the close-range view 1640 may provide an analysis of facial read levels 1656. The facial read levels may be a determination based on various facial features, such as facial expressions, color, and motion of individual facial features. For example, in the illustrated embodiment, the close-range view provides a representation 1660 of the color, eyes, and mouth levels. The representation may include a number line with each end of the spectrum representing an approachable or non-approachable indication. In some embodiments, the representation may be color-coded and/or utilize symbols to indicate to the user the emotional state of the observed individual.

FIG. 16C illustrates another such display view containing information that can be seen on the display device 1108, 1208. The illustrated embodiment depicts a recommendation view 1680 that provides information relating to the recommend social response the social aid system 1100 may provide to the user. The recommendation view 1680 may provide a recommendation indication 1684 to trigger the user to act according to the instructions on the display. In some instances, the recommendation view 1640 may comprise an indication 1688 of the observed individual's emotional state. The recommendation view 1680 provides a recommendation summary 1698. The recommendation summary 1698 may include biographical information relating to the observed individual along with the associated recommended social response.

The social aid system 1100 may include a series of steps intended to train a user from an initial training state. The initial training state may rely heavily on the social aid system 1100 to process social cues. At this stage, the user may require the social aid system 1100 to convey the social state information to the user. This stage occurs while the user is interacting with the observed individual being scanned by the social aid system 1100. In this stage, the user may receive multiple types of information concurrently. The information may relate to the user's own visual and audio tracks, along with information processed and projected on the display device 1108, 1208. The combination of the user and social aid system 1100 information provides the user to develop a correlation between the user and system information. The learned correlation provides a foundation to permit the user to begin learning to read social cues.

The social aid system 1100 may include a second step to assess the user's social skills. The social aid system 1100 may diminish or delay the information the social aid system 1100 provides to the user. This may allow the user to arrive at their own social state conclusion. The user may then compare it with the recommendation provided by the social aid system 1100. When the user's skills are sufficiently improved, the user may transition to a less invasive social aid system 1100.

The third step of the social aid system 1100 may expose the user to real world social interaction. In some embodiments, the user may choose to halt any assistance from the social aid system 1100. Alternatively, the social aid system 1100 may utilize a less intrusive variant of the social aid system 1100. For example, a less intrusive variation may include glasses with display window or a mobile device running the social aid system 1100 software to process information from a wearable camera (as shown in FIG. 13).

Combination and/or Subcombination Embodiments

Although features of the smart injection system are described individually in various embodiments herein, a skilled artisan will appreciate that any one or more of those features described herein can be implemented on a smart injection system.

An example combination of features and the advantages thereof are illustrated in FIG. 9. The injection system can have an electronic assembly configured to measure a variety of information, including but not limited to force of injection and/or travel of the stem information, angular and relative position of the stem relative to a patient's face, verify authenticity and other product information of a prefilled syringe, and verify identity of an injector, in the manners described above. The information measured by the electronic assembly can be transmitted to one or more processors located locally or remotely. In some embodiments, the measured data can cause the one or more processors to generate local alerts/alarms on the injection system or in the room where the patient receives the injection. In some embodiments, data transmission can be performed wirelessly and the one or more processors can be located on one or more remote servers (the "Cloud"). In response to the measured data, the processor can output instructions to the injection system. Examples of the instructions include information about whether the injector is an authorized/licensed medical professional, whether the procedure is in compliance with protocols, whether the medication being injected is safe and/or authentic, and the like. In response to the measured data, the processor can also output alerts and/or data to the manufacturer, including but not limited to information about medication usage for inventory control, monitoring of injectors' qualification, and injection quality data. In some embodiments, the processor can make the alerts and/or data available for retrieval by the manufacturer. In other embodiments, the processor can automatically send the alerts and/or data to the manufacturer.

In addition, an augment to the alarms/alerts on the injection system can provide audio, visual or tactile feedback confirming the correct injection technique. This continuous feedback contributes to a more perfect injection than threshold alarms that are triggered only at the limits of acceptable operation.

It is to be understood that the various sensor and electronics, as well as the techniques and processes described with respect to each embodiment disclosed herein can be used with and integrated to other embodiments disclosed herein as would be readily understood by a person of skill in the art reading the present disclosure.

Terminology

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Any methods disclosed herein need not be performed in the order recited. The methods disclosed herein include certain actions taken by a practitioner; however, they can also include any third-party instruction of those actions, either expressly or by implication. For example, actions such as "inserting the testing tool" include "instructing insertion of a testing tool."

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid state storage devices, disk drives, etc.). The various functions disclosed herein may be embodied in such program instructions, and/or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state. In some embodiments, the computer system may be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on general purpose computer hardware, or combinations of both. Various illustrative components, blocks, and steps have been described above generally in terms of their functionality. Whether such functionality is implemented as specialized hardware versus software running on general-purpose hardware depends upon the particular application and design constraints imposed on the overall system. The described functionality can be implemented in varying ways for each particular application, but such implementation decisions should not be interpreted as causing a departure from the scope of the disclosure.

Moreover, the various illustrative logical blocks and modules described in connection with the embodiments disclosed herein can be implemented or performed by a machine, such as a general purpose processor device, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. The scope of certain embodiments disclosed herein is indicated by the appended claims rather than by the foregoing description. All changes which come within the meaning and range of equivalency of the claims are to be embraced within their scope.

What is claimed is:

1. An injection aid system configured to aid a live patient injection, the system comprising:
a computing system comprising at least one processor and a memory device, the computing system configured to receive imaging data of a live patient and generate a three-dimensional virtual model based on the imaging data, the three-dimensional virtual model including likeness of under-skin anatomical features of the live patient; and
a display device coupled to the computing system, the display device configured to be worn by a user performing the live patient injection,
wherein the at least one processor is configured to merge the imaging data of the live patient with a position of the live patient relative to the display device such that when the user is facing the live patient, information projected by the display device is superimposed on a field of view of the user and on the live patient, wherein the information comprises the three-dimensional virtual model of the imaging data such that the user can see an outline of a treatment target on the live patient with a projection of the three-dimensional virtual model superimposed within the treatment target.

2. The injection aid system of claim 1, wherein the information relates to at least one or more of a medication type, injection locations, needle angles, needle depth, or medication volume.

3. The injection aid system of claim 1, wherein the likeness of under-skin anatomical features of the live patient comprise at least one or more of arteries, veins, fat, muscles, or nerves.

4. The injection aid system of claim 1, wherein the computing system is further configured to determine a location of hazard zones based on the imaging data.

5. The injection aid system of claim 4, wherein the computing system is further configured to cause the display device to display the location of hazard zones to avoid misplaced medication or resulting harm.

6. The injection aid system of claim 1, further comprising a scanner, the scanner configured to determine the position of the live patient relative to the display device.

7. The injection aid system of claim 1, wherein the information further comprises changes to at least part of the live patient's anatomy during the injection performed by the user.

8. The injection aid system of claim 1, wherein the information further comprises information in the form of numerical values, colored shapes, bar charts, or grids.

9. The injection aid system of claim 1, wherein the display device comprises a stereoscopic display.

10. The injection aid system of claim 9, wherein the display device comprises a pair of augmented reality glasses.

11. A method of aiding a live patient injection, the method comprising:
using a computing system comprising at least one processor and a memory device:
receiving imaging data of a live patient;
generating a three-dimensional virtual model based on the imaging data, the three-dimensional virtual model including likeness of under-skin anatomical features of the live patient;
determining recommended injection information based at least in part on the imaging data of the live patient; and
causing a display device coupled to the computing system to display the recommended injection information and merging the imaging data of the live patient with a position of the live patient relative to the display device such that the displayed recommended injection information is superimposed on the live patient, the display device configured to be worn by a user performing the live patient injection such that when the user is facing the live patient, the user is able to perform the injection guided by the displayed recommended injection information without having to look away from the live patient,
wherein the displayed recommended injection information comprises the three-dimensional virtual model of the imaging data such that the user can see an outline of a treatment target on the live patient with a projection of the three-dimensional virtual model superimposed within the treatment target.

12. The method of claim 11, wherein the recommended injection information further comprises at least one or more of a medication type, injection locations, needle angles, needle depth, or medication volume.

13. The method of claim 11, wherein the recommended injection information further comprises changes to at least part of the live patient's anatomy during the injection performed by the user.

14. The method of claim 11, wherein the likeness of under-skin anatomical features of the live patient comprises at least one of arteries veins, fat, muscles, or nerves, the recommended injection information comprising the under-skin anatomical features.

15. The method of claim 14, further comprising determining a location of hazard zones based on the imaging data.

16. The method of claim 15, further comprising causing the display device to display the location of hazard zones to avoid misplaced medication or resulting harm.

17. The method of claim 11, wherein the display device comprises a stereoscopic display.

18. The method of claim 17, wherein the display device comprises a pair of augmented reality glasses.

19. The method of claim 11, wherein the recommended injection information further comprises information in the form of numerical values, colored shapes, bar charts, or grids.

* * * * *